(12) United States Patent
Li et al.

(10) Patent No.: US 7,983,874 B2
(45) Date of Patent: Jul. 19, 2011

(54) SIMILARITY INDEX: A RAPID CLASSIFICATION METHOD FOR MULTIVARIATE DATA ARRAYS

(75) Inventors: Boyan Li, Galay (IE); Alan G. Ryder, Galway (IE)

(73) Assignee: National University of Ireland, Galway, Galway (IE)

( * ) Notice: Subject to any disclaimer, the term of this patent is extended or adjusted under 35 U.S.C. 154(b) by 355 days.

(21) Appl. No.: 12/157,365

(22) Filed: Jun. 10, 2008

(65) Prior Publication Data

US 2009/0306932 A1    Dec. 10, 2009

(51) Int. Cl.
*G06F 17/18*   (2006.01)
*G06F 17/40*   (2006.01)

(52) U.S. Cl. ............................ 702/179; 702/32; 708/806

(58) Field of Classification Search .................. 702/179, 702/28, 30, 32
See application file for complete search history.

(56) References Cited

U.S. PATENT DOCUMENTS

| | | | |
|---|---|---|---|
| 6,341,257 B1 * | 1/2002 | Haaland | 702/27 |
| 6,904,384 B2 * | 6/2005 | Tai | 702/179 |
| 7,062,417 B2 * | 6/2006 | Kruger et al. | 703/2 |
| 7,526,405 B2 * | 4/2009 | Miller | 702/179 |
| 2005/0043902 A1 * | 2/2005 | Haaland et al. | 702/30 |

OTHER PUBLICATIONS

Poster Presentation at conference held on Jun. 11-14, 2007, 1 page.
Anderson, C.M., et al., Practical aspects of PARFAC modeling of flourescence excitation-mission data, Journal of Chemometrics, 2003; 17: 200-215.
Bro, Rasmus, Review of Multiway Analysis in Chemistry—2000-2005, Critical Review in Analytical Chemistry, 36: 279-293, 2006.

\* cited by examiner

*Primary Examiner* — Hal D Wachsman
(74) *Attorney, Agent, or Firm* — Jackson Walker L.L.P.

(57) ABSTRACT

Provided herein is a method of determining the similarity between a first multivariate data set and a second multivariate data set. The method may be applied to rapidly assess the similarity between fluorescence spectroscopy multivariate data sets in quality control analysis. The method includes representing the data of a first and a second multivariate data set in matrix form to yield a multivariate data matrix and calculating the magnitude of an additive and subtractive combination of each multivariate data matrix. The concept of a penalty parameter is introduced to set a detectable limit of variance between the first multivariate data set and the second multivariate data set and the penalty parameter is used in combination with the magnitude of an additive and subtractive combination of each multivariate data matrix to determine a similarity value.

21 Claims, 12 Drawing Sheets

SIMILARITY INDEX: A RAPID CLASSIFICATION METHOD FOR MULTIVARIATE DATA ARRAYS

FIELD OF THE INVENTION

The present invention relates to the quantitative and qualitative analysis of materials or chemicals based on comparing the similarity of multivariate data sets that are generated by spectroscopic, chromatographic, or imaging means.

BACKGROUND TO THE INVENTION

As used herein, boldface capitals designate two-dimensional data matrices (e.g., $X_{I \times J}$) and underlined boldface capitals symbolize three-way arrays (e.g., $\underline{X}_{I \times J \times K}$). Vectors are represented by bold lowercase characters, scalars or elements of matrices by lowercase italics. The superscript T denotes the matrix or vector transposition. $\|X\|_p$ indicates the Entrywise p-norm of matrix X, where $p \geq 1$.

The analysis of complex aqueous based mixtures such as cell culture media, fermentation broths, wastewater, river/sea water etc. is often difficult when the compositional differences between samples are very small. For example, cell culture broth is an enormously complex mixture consisting of a vast variety of components at low concentrations (e.g., amino acids, peptides, sugars, proteins, vitamins, and metals). The concentration profiles of the components vary widely during the course of the cultivation or fermentation. A key challenge therefore is the rapid characterization of compositional changes, in the gross sense and for specific analytes. The solution is usually different for each of component of the mixture, and therefore requires the use of a range of analytical technologies and techniques. Many current methods, for example, in monitoring compositional changes of a process broth or the production of the product (e.g., the biotherapeutic in biopharmaceutical industry) during:manufacture are slow, e.g., typically hours or days. Thus, there is a need for the development of rapid analytical methods that can characterize constituents in cell culture media and provide useful information on cell culture progress. This need consists of two elements: one to monitor the use/level of constituents of cell culture media, and the other, product formation. One way in which rapid analyses for gross compositional changes can be achieved is via the use of multidimensional spectroscopy based methods. However, in many cases the differences in the spectra are very small and assessing these small changes in the topography of multidimensional spectra can be difficult and time-consuming.

Fluorescence spectroscopy is widely used in biomedical, biopharmaceutical, chemical, environmental, food, and other industrial domains. Fluorescence has proven itself as a highly sensitive and potentially selective analytical technique capable of measuring analyte concentrations down to sub-nanomolar levels in routine use. In fluorescence spectroscopy, the fluorescence properties can be measured by recording measurements spanning both the excitation and emission wavelengths of the mixture. Collating a series of emission scans from a range of excitation wavelengths produces an excitation-emission matrix (EEM). Such an EEM spectrum can be visualized as a two-dimensional contour map or as a three-dimensional landscape. Another possibility is total synchronous fluorescence scan (TSFS) spectrum, which is obtained by scanning both emission and excitation properties simultaneously. When a group of EEMs (or TSFS data) of equal excitation and emission wavelengths are coupled with each other, a three-way data array (for example as a matrix with samples×excitation×emission dimensions) is generated. There are a great number of applications using fluorescence EEM information for the characterization of analytes, and the most of them have frequently involved its combination with multiway multivariate analysis methods such as multiway principal component analysis (MPCA), N-way partial least squares (NPLS), and parallel factor analysis (PARAFAC). However, these methods require a deep mathematical knowledge and expertise to undertake the complex procedures involved. This can in turn hinder the capability of an analyst to faithfully conduct these methods using large amounts of data.

The Matrix congruence coefficient (MatrixCC) can be thought of as describing a similarity matrix of all the variables involved in the numerator term in the following formula, $$MatrixCC = \frac{\|X_1^T X_2\|_2}{\|X_1\|_2 \|X_2\|_2} \tag{1}$$

Each score of $X_1^T X_2$ expresses the similarity between two data points of matrices $X_1$ and $X_2$, which is strongly related to the data counterparts. The denominator terms normalize the similarity results obtained. Higher scores are given to more similar characters, and lower or negative scores for dissimilar characters. Formula (1) is based in molecular electrostatic potential comparison and structural alignment. For instance, the similarity/dissimilarity of two compared molecules in terms of their relevant target matrices assigns identical bases a score of +1 and non-identical bases a score of zero or −1 in a simple way.

In essence, the MatrixCC is a congruence angle between two spectral hyperplanes spanned by $X_1$ and $X_2$, which measures their linear correlation degree. Generally, this calculation tends to give higher similarity values when the common feature predominates both the matrices $X_1$ and $X_2$. However, sometimes the MatrixCC method fails to describe/identify differences of interest in complex mixtures where the concentration of the individual constituents can vary significantly. In other words, the sensitivity of the MatrixCC method may not be sufficient for complex mixture analysis.

Multiway principal component analysis (MPCA) is statistically and algorithmically consistent with standard PCA, and has the same goals and benefits. The philosophy behind them is multivariate statistical projection, in which a large data set of highly correlated variables is projected into a low-dimensional spaceahat summarizes the variables within a set of suboptimal principal components (PCs). Thus, the original data are compressed and the relevant information is extracted at the same time. PCA describes a two-dimensional data matrix X of m observations by n variables in an underlying factor analytic manner, $$X = U \Sigma V^T \tag{2}$$

where U is a m-by-m orthogonal matrix, V is a n-by-n orthogonal matrix, and $\Sigma$ is a m-by-n matrix containing non-negative real singular values of decreasing magnitude along its main diagonal ($\sigma_1 \geq \sigma_2 \geq \ldots \geq \sigma_{min(m,n)} \geq \ldots \geq 0$), and zero off diagonal elements. This process can be realized by the singular value decomposition (SVD) of X.

In order to optimally capture the variations of the data while minimizing the noise effect corrupting the PCA representation, the loading vectors corresponding to the F largest singular values are typically retained. For each loading vector, the amount of variance explained by the PCA model is calculated via comparing the estimates $\sigma_i^2 (i=1, 2, \ldots, F)$ computed by the model with the true data ($\Sigma\sigma^2$), $$\text{Explained variance } (\%) = \frac{\sigma_i^2}{\Sigma\sigma^2} \times 100 \quad (3)$$

$$(i = 1, 2, \ldots, F)$$

Then, these F vectors are stacked into a n-by- F loading matrix P (generally called loadings). For the score space, the Hotelling $T^2$ statistic can be calculated from the PCA representation:

$$T^2 = x^T P \Sigma_F^{-2} P^T x \quad (4)$$

where x is an observation of X, whose dimension is (n×1), and $\Sigma_F$ contains the first F rows and columns of $\Sigma$. The threshold for the $T^2$ statistic is given as, $$T_\alpha^2 = \frac{F(m-1)(m+1)}{m(m-F)} F_\alpha(F, m-F) \quad (5)$$

In Eq. (5), $\alpha$ means a significant level tested for F-distribution, for instance, $\alpha=0.05$.

MPCA, by its nature, is an extension of PCA capable of handling multiway data. Hereafter, MPCA is equivalent to unfolding a three-way array $\underline{X}_{I \times J \times K}$, of which the fluorescence EEMs are generated from K measurements at I excitation and J emission wavelengths, or of TSFS data at I Delta and J excitation wavelengths, slice by slice, rearranging these slices into a large two-dimensional matrix X and then performing a standard PCA. For an MPCA analysis of K measurements, a most meaningful approach is to unfold the data array $\underline{X}$ into a matrix X with dimensions (IJ×K). The similarity and variability among the K measurements can be assessed by the analysis of their scores and Hotelling $T^2$ statistics within the model. MPCA has been extensively applied to statistic process monitoring and multivariate quality control.

PARAFAC and its variant PARAFAC2 are one of the simplest generalizations of multiway multivariate curve resolution. Its trilinear methodology is based upon the principle of proportional profiles. An in-depth description of PARAFAC can be found in the scientific literature. An F-component (or factor) PARAFAC model on an EEM data array $\underline{X}_{I \times J \times K}$ can be formulated as, $$x_{ijk} = \sum_{f=1}^{F} a_{if} b_{jf} c_{kf} + e_{ijk} \quad (6)$$

$$(i = 1, 2, \ldots, I; j = 1, 2, \ldots, J; k = 1, 2, \ldots, K)$$

where $x_{ijk}$ is the intensity of the kth measurement/sample at the ith excitation and jth emission wavelengths, $a_{if} b_{jf} c_{kf}$ are parameters describing the behaviors of the excitation, emission variables, and samples of F components. The residuals $e_{ijk}$ contain the errors and the part not captured by the model. Analogous to the decomposition form of standard PCA, the PARAFAC model can be written in matrix notation, $$X_k = A_{I \times F} \text{diag}(c_k) B_{J \times F}^T + E_k \ (k=1 \ldots K) \quad (7)$$

Here $X_k$ is the kth frontal slice of $\underline{X}_{I \times J \times K}$, which corresponds to the EEM of the kth measurement. The F-vector $c_k$ is the kth row of matrix C. The matrices A, B, and C hold the estimated excitation, emission, and concentration information of the underlying sample constituents, respectively.

Rather than MPCA focusing only on the variance of the EEM data, PARAFAC focuses on profiling the contributions of each constituent. If the data are approximately trilinear and the correct number of components (viz. F) is used, the I-vector $a_f (f=1,2, \ldots, F)$ with elements $a_{if} (i=1,2, \ldots, I)$ is the estimated excitation spectrum of constituent f in sample k, and likewise $b_f$ is the estimated emission spectrum of this constituent. The scores in $c_{kf}$ of the F-vector $c_k$ may be interpreted as the relative concentration of constituent f in sample k. The PARAFAC performance is assessed based on the sum of squared errors, $$\min\left(\sum_{i,j,f=1}^{I,J,F} e_{ijk}^2\right) \quad (8)$$

The popularity of PARAFAC for chemical and industrial applications lies in the facts that it generates a unique model, the model results can be interpreted in a meaningful way to provide information on constituent concentrations, and that the results are robust by virtue of being calculated using least square methods. However, in practice, the data arrays are usually contaminated by noise and other factors (e.g. Rayleigh scattering in fluorescence spectroscopy) which induce deviations from the trilinear prerequisite for PARAFAC. As a result of the presence of deviations in the spectral data, the PARAFAC model becomes less precise (it no longer yields a unique solution), and this may generate misleading estimated parameters (the spectral and concentration profiles). Such inaccuracy can be formulated as:

$$\underline{X} = \underline{X}(A, B, C) + \underline{D}_{independent} + \underline{D}(A, B, C) + \underline{E} \quad (9)$$

In which X(A, B, C) contains the linear responses of compositions, D(A, B, C) denotes deviations with a certain relationship to the three parameter matrices A, B, and C, $D_{independent}$ represents deviations independent of A, B, and C, and E holds the residual variation.

For the data arrays of which D(A, B, C)≠0, it is not usually possible for PARAFAC to directly estimate a reliable solution to the model parameters unless some pretreatments are used beforehand. If the data arrays satisfy the D(A, B, C)=0 condition, then the influence of $D_{independent}$ on the accuracy of the estimated model parameters can be mitigated by imposing some constraints on the model, such as non-negativity and/or incorporation of a priori information (e.g., the known concentrations) into the decomposition procedure.

OBJECT OF THE INVENTION

The present invention demonstrates a novel, facile analytical method of similarity index (henceforward called SimI) suitable for the rapid analysis of complex data sets. In one particular embodiment the method enables comparative complex aqueous media to be evaluated rapidly and quantitatively as to the resultant variance in the topography of different multidimensional fluorescence data and the compositional consistency of samples. The efficacy of this method is demonstrated using a theoretical framework, a model dataset of EEM and TSFS spectra from various 8-Hydroxypyrene-1,3, 6-Trisulphonic acid (HPTS) solutions, and the fluorimetric analyses of cell culture media from different bioprocess lots and batches.

SUMMARY OF THE INVENTION

The present invention provides for a method of determining the similarity between a first multivariate data set and a second multivariate data set comprising:
i) representing the data of each multivariate data set in matrix form to yield a multivariate data matrix, wherein each multivariate data matrix has the same dimensions;
ii) calculating the magnitude of an additive and subtractive combination of each multivariate data matrix;
iii) introducing a penalty parameter to set a detectable limit of variance between said first multivariate data set and said second multivariate data set, and using said penalty parameter in combination with the results of step ii) to determine a similarity value;
wherein said determined similarity value indicates the variance between said first multivariate data set and said second multivariate data set.

The method of the present invention allows for rapid classification and analysis of multivariate data sets.

Desirably, the step of calculating the magnitude of an additive and subtractive combination of each multivariate data matrix may comprise calculating the entrywise p-norm of an additive and subtractive combination of each multivariate data matrix, wherein $p \geq 1$. For example, wherein $p=1$ or $p=2$.

The penalty parameter associated with the method of the present invention may be expressed as a function of a threshold similarity value and said detectable limit of variance between said first multivariate data set and said second multivariate data set. Desirably, the penalty parameter is determined by:
a) subtracting a threshold similarity value from the integer 1;
b) selecting a detectable limit of variance between said first multivariate data set and said second multivariate data set;
c) adding the detectable limit of variance to the integer 2, and dividing the result by the detectable limit of variance; or
d) subtracting the detection limit of variance from the integer 2, and dividing the result by the detection limit of variance; and
e) multiplying the results of steps a) and c) or multiplying the results of steps a) and d).

In one embodiment of the method of the present invention the similarity value is determined by:
a) multiplying the penalty parameter by the magnitude of a subtractive combination of the multivariate data matrices;
b) subtracting the result of step a) from the magnitude of an additive combination of the multivariate data matrices; and
c) dividing the result of step b) by the magnitude of an additive combination of the multivariate data matrices.

In a further embodiment of the method of the present invention the similarity value is determined by:
a) multiplying the penalty parameter by the entrywise p-norm of a subtractive combination of the multivariate data matrices;
b) subtracting the result of step a) from the entrywise p-norm of an additive combination of the multivariate data matrices; and
c) dividing the result of step b) by the entrywise p-norm of an additive combination of the multivariate data matrices.

The method of the present invention also provides for when the data of the multivariate data sets are discrete representations of multivariate observations. In such a circumstance, and when the step of calculating the magnitude of an additive and subtractive combination of each multivariate data matrix comprises calculating the entrywise p-norm of an additive and subtractive combination of each multivariate data matrix, the entrywise p-norm may be computed as a summation.

The method of the present invention extends to embodiments wherein the multivariate data sets are generated by spectroscopic, chromatographic, or imaging means. As used herein spectroscopic means includes data collected from techniques based on, for example, Fluorescence Excitation-Emission spectroscopy, Infra-Red (IR) absorption, Raman scattering, Near-Infra-Red (NIR) absorption, and Nuclear Magnetic Resonance (NMR). Chromatographic means comprises data;collected from techniques based on, for example, Gas Chromatography (GC), High Performance Liquid Chromatography (HPLC), Ultra-High Performance Liquid Chromatography. Reference to an 'imaging means' comprises any process that generates a 2-Dimensional (pixel by pixel) or 3-Dimensional (voxel by voxel) image suitable for processing in the method of the present invention.

Desirably, the method of the present invention is directed to processing spectroscopy multivariate data sets. Further desirably, the spectroscopy multivariate data sets may comprise fluorescence spectroscopy multivariate data sets. For example, the multivariate fluorescence spectroscopy data sets may, comprise Fluorescence Excitation-Emission Matrix data sets or Total Synchronous Fluorescence Scanning data sets, Time-Resolved Fluorescence Emission Spectra data sets and other related methodologies. Desirably, the multivariate fluorescence spectroscopy data sets will have been processed to correct the effects of Rayleigh scattering, Raman scattering and combinations thereof.

In a further embodiment of the present invention wherein the multivariate data sets comprise fluorescence spectroscopy multivariate data sets the step of calculating the magnitude of an additive and subtractive combination of each multivariate data matrix may comprise calculating the entrywise p-norm of an additive and subtractive combination of each multivariate data matrix, wherein $p \geq 1$. Preferably, $p=1$ or $p=2$. Further preferably, where $p=2$. For a fluorescence spectroscopy multivariate data set the similarity value may be determined by:
a) multiplying the penalty parameter by the 2-norm of a subtractive combination of the multivariate data matrices;
b) subtracting the result of step a) from the 2-norm of an additive combination of the multivariate data matrices;
c) dividing the result of step b) by the 2-norm of an additive combination of the multivariate data matrices.

The method of the present invention further provides for wherein the data are discrete representations of multivariate observations. In such a circumstance the 2-norm is computed as a double summation.

In the embodiment where the multivariate data sets comprise fluorescence spectroscopy multivariate data sets the penalty parameter may be expressed as a function of a threshold similarity value and said detectable limit of variance between said first multivariate data set and said second multivariate data set. Desirably, the penalty parameter is determined by:
a) subtracting a threshold similarity value from the integer 1;
b) selecting a detectable limit of variance between said first multivariate data set and said second multivariate data set;

c) adding the detectable limit of variance to the integer 2, and dividing the result by the detectable limit of variance; or d) subtracting the detection limit of variance from the integer 2, and dividing the result by the detection limit of variance; and e) multiplying the results of steps a) and c) or multiplying the results of steps a) and d).

The value of the penalty parameter may be selected from 0.5, 1, 2, 3, 4, 5, 6 or 8.

The method of the present invention may be used in quality control or chemical analysis.

In a further embodiment the invention provides for a processing means for performing the method of the present invention. In yet a further embodiment, the invention is directed to a computer readable medium having instructions, which when executed by a processor, performs the method of the present invention.

BRIEF DESCRIPTION OF THE DRAWINGS

Additional features and advantages of the present invention are described in, and will be apparent from, the detailed description of the invention and from the drawings in which.

DETAILED DESCRIPTION OF THE INVENTION

Figure 1:
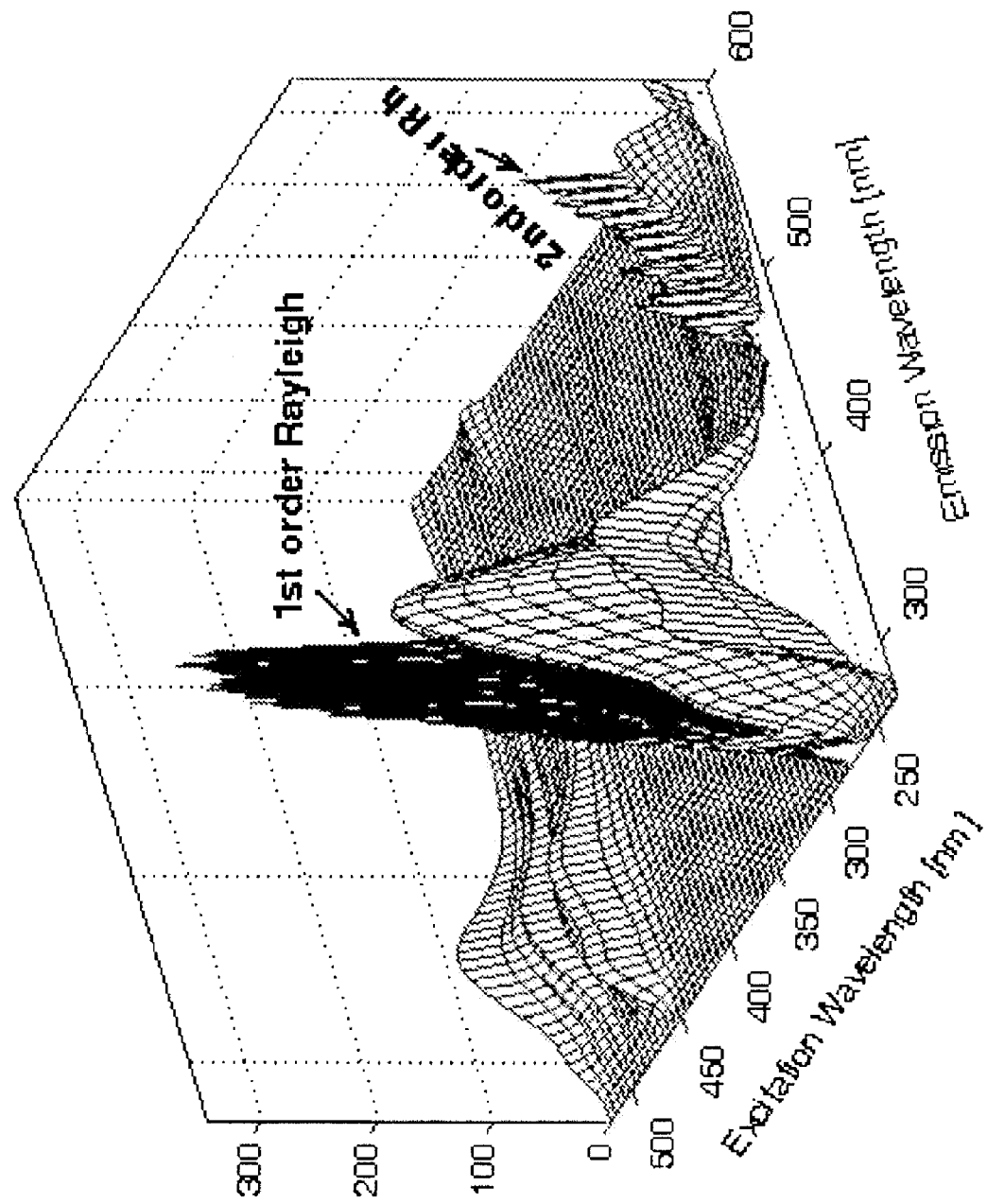
FIG. 1 illustrates a typical multidimensional fluorescence landscape plot showing the fluorescence properties of an aqueous based sample as a function of excitation and emission wavelengths. The marked peaks are the 1st- and 2nd-order Rayleigh scattering peaks.

The particular embodiment discussed below relates to a first and a second multivariate fluorescence spectroscopy data set. Given two fluorescence EEM or TSFS data matrices $X_1$ and $X_2$ of size (I×J), the idea of the Similarity index (SimI) is conceptualized as below, $$SimI = \frac{\|X_1 + X_2\|_p - \lambda\|X_1 - X_2\|_p}{\|X_1 + X_2\|_p} = 1 - \lambda\frac{\|X_1 - X_2\|_p}{\|X_1 + X_2\|_p} \tag{10}$$

If p is odd (e.g., p=1, 3, 5, etc.), desirably the absolute value (ABS) operation will be done on the elements of $p_{x_1-x_2}$ and $p_{x_1+x_2}$ of the matrices $(X_1-X_2)$ and $(X_1+X_2)$. That is, $\|ABS(X_1-X_2)\|_{p=1,3,5}$ and $\|ABS(X_1+X_2)\|_{p=1,3,5}$. If the ABS operation is n first done when p=1, 3, 5, etc., then the modulus (magnitude) of the p-norm of the straightforward additive and subtractive combination of each multivariate data matrix would be overly complex. As a result, it may be difficult to define both the appropriate penalty parameter and similarity threshold, which may not enable the SimI method to perform very well. If p is even (e.g., p=2, 4, 6, etc.), the abovementioned problem does not factor. When p=2, 4, 6, etc. the p-norm operation works similar to the ABS operation. This avoids the possible complexity of the resulting modulus (magnitude) from the p-norm of the elements of any matrix $(X_1-X_2)$ or $(X_1+X_2)$.

The embodiment discussed herein concentrates on the 2-norm/Frobenius norm (i.e., p=2) for the SimI method, thus, Eq. (10) is re-written, $$SimI = \frac{\|X_1 + X_2\|_2 - \lambda\|X_1 - X_2\|_2}{\|X_1 + X_2\|_2} \tag{11}$$

$$= 1 - \lambda \frac{\left(\iint p_{x_1-x_2}^2 dv\right)^{1/2}}{\left(\iint p_{x_1+x_2}^2 dv\right)^{1/2}}$$

where $p_{x_1-x_2}$ and $p_{x_1+x_2}$ are elements of two I-by-J matrices $(X_1-X_2)$ and $(X_1+X_2)$, respectively, which are generated from $X_1$ and $X_2$ being compared, such that, $$p_{x_1-x_2}=x_{ij,1}-x_{ij,2},\ p_{x_1+x_2}=x_{ij,1}+x_{ij,2} \tag{12}$$

$x_{ij,1}, x_{ij,2}$ are the spectral responses of $X_1$ and $X_2$, respectively. i=1,2,..., I and j=1,2,..., J signify the excitation (Ex) and emission (Em) wavelengths for taking the EEM spectrum. For the TSFS data, j=1,2,..., J points to the Delta (Δ) wavelength. λ is a penalty parameter, and can be adopted to define a significant threshold level. In the present study, λ=4 is used in practice, which enables the SimI method to identify around 5% variance in the topographies of multidimensional fluorescence data related to the compositions of aqueous media samples.

If the data are discrete representations of multivariate observations instead of continuously observed functions, then the SimI can be computed, $$SimI = 1 - \lambda \frac{\left(\sum_{i=1}^{I}\sum_{j=1}^{J} p_{x_1-x_2}^2\right)^{1/2}}{\left(\sum_{i=1}^{I}\sum_{j=1}^{J} p_{x_1+x_2}^2\right)^{1/2}} \tag{13}$$

Generally, SimI≦1. The closer the SimI value is to 1, the more similar $X_1$ and $X_2$ concerning with their data topographic structures, and the more correlated they are. As the matrix $X_1$ becomes more dissimilar to $X_2$, their SimI becomes a larger negative value.

In the particular case of the SimI, it is described in terms as follow, i) If $X_1=0$ or $X_2=0$, then SimI=0, ii) If $X_1=X_2$, then SimI=1, iii) If $\|X_1+X_2\|_2<\|X_1-X_2\|_2$, then SimI<0, which infers that the spectra $X_1$ and $X_2$ are very dissimilar, and therefore the original source samples are different.

This index signifies whether the two measured objects $X_1$ and $X_2$ may correlate to each other and how similar they are. The similarity can be ascribed to not only their common feature $(X_1+X_2)$ but also the variance $(X_1-X_2)$ with respect to the spectral topographies (i.e., the data structure and peak-related position).

EXPERIMENTAL

Materials

8-Hydroxypyrene-1,3,6-trisulphonic acid (HPTS) powder was purchased from Molecular Probes, Eugene, Oreg., USA. Sodium hydrogen phosphate heptahydrate ($Na_2HPO_4.7H_2O$) and sodium dihydrogen phosphate monohydrate ($NaH_2PO_4.H_2O$) were purchased from Sigma-Aldrich, Inc., UK. Cell culture media samples were provided by a pharmaceutical company and originate from a biopharmaceutical process.

Sample Preparation

A 0.2 M phosphate buffer solution was first prepared by adding 2.3316 g of $Na_2HPO_4.7H_2O$ powder and 0.1788 g of $NaH_2PO_4.H_2O$ powder into 50 mL Millipore water. Then, 0.0131 g of HPTS powder was dissolved in 100 mL Millipore water, which gave a primary stock solution of HPTS. Finally, 10 mL of the primary stock solution was mixed with the entire above-prepared buffer solution as well as Millipore water to make up to a 100 mL of secondary stock solution.

Case study 1: The secondary stock solution was diluted by Millipore water to produce a $1.375 \times 10^{-6}$ M working solution of HPTS in phosphate buffer, whose pH was 7.6. Of this working solution, forty-nine separate measurements were made for the EEM and TSFS data collection over thirteen days. HPTS is a fluorophore whose emission properties are very sensitive to changes in acidity (pH value), hence the need for a buffered solution.

Case study 2: A series of HPTS solutions in phosphate buffer at ten different concentration levels were prepared by diluting the secondary stock solution with Millipore water. They are summarized in Tables 1A-1B.

Case study 3: Forty-five EEM spectra of a $1.375 \times 10^{-6}$ M working solution of HPTS in phosphate buffer measured over twelve days as in Case study 1 were utilized as a set of seeds. A variation amounting to 3.0, 4.0, 5.0, 6.0, and 7.0% of the fluorescence intensity was individually forced on these seeds to generate five EEM simulation scenarios. For each of these five scenarios, zero-mean Gaussian noise with 0.2% standard deviation (or uncertainty) was randomly augmented into 1800 simulated EEM data. In such a way, another five TSFS simulation scenarios were also generated.

Case study 4: 112 samples of cell culture media supplied by a Pharmaceutical company were used to demonstrate the efficacy of the method to identify significant outliers. These samples had been made up in batches and stored under sterile conditions for varying timeframes before being sampled. Prior to usage, the cell culture media were diluted in a certain proportion with Millipore water to reduce concentration effects on the fluorescence spectra. All the preparations were made in a sterile bio-safety vertical laminar flow hood (NU-126-400E, NuAire Corp., USA).

Instrumentation

The fluorescence spectra of the HPTS solutions and cell culture media samples were measured by with a Cary Eclipse fluorescence spectrophotometer (Varian, Inc., Australia). The fluorescence EEM data were recorded over an excitation range of 230~520 nm and emission range of 270~600 nm. A 5 nm interval was co-added for both the excitation and emission scanning. Another Delta ($\Delta$) range of 5~200 nm also with a 5 nm interval was used for the TSFS data collection. Semi micro quartz cuvettes (Lightpath Optical Ltd., UK) with an excitation path length of 10 mm were employed for all the fluorescence measurements, and the spectral background was taken from Millipore water in quartz cuvette at the beginning and end of each data collection batch. All experiments were performed at room temperature, and all the HPTS solutions and cell culture media used were stored in a temperature controlled (2~4° C.) pharmacy refrigerator (LEC Refrigeration Plc, UK).

Data analysis

The algorithms were implemented using a technical computing or mathematics software product such as MATLAB (The MathWorks, Inc., USA) version 7.4 for Windows. PLS_toolbox 4.0 (Eigenvector Research, Inc., USA) and in-house-written procedures were used for the various data analysis steps involved. All calculations were performed using a standard personal computer.

Rayleigh Scattering

Fluorescence EEMs are often spectrally contaminated by Rayleigh and Raman scattering effects. These two types of scatter originate from the interaction between molecules in the sample and the incident light. Rayleigh scatter is caused by molecules of the sample oscillating at the same frequency as the excitation light, and thus the light emitting at the same wavelength as the excitation gives rise to first-order Rayleigh, second-order Rayleigh scatter at the emission wavelength equals twice the excitation, and also at higher multiples of the wavelength. Raman scatter is a result of non-elastic scattering from molecules in the sample. The Raman peaks are shifted in energy relative to the Rayleigh scatter peak, and the Stokes shifted peaks tend to overlap with fluorescence spectra. In the context of aqueous samples, the primary Raman band observed is the O—H stretching mode at ~3400 $cm^{-1}$. FIG. 1 shows an example of Rayleigh scattering, which occurred in a fluorescence EEM of aqueous cell culture media. The first order Rayleigh scattering is several times more intense than the second order scattering.

Since Rayleigh and Raman scatter are generally unrelated to the chemical composition (or more specifically the species that give rise to the fluorescence signals) of dilute aqueous samples, and the scatter peaks do not behave linearly (or trilinearly), they may complicate and bias modeling of the fluorescence data unless care is taken. There are two typical strategies to mitigate the effect of scattering signals. One is to select a specific range of wavelengths for data acquisition avoiding the spectral regions which include scatter peaks, and the other is to mathematically remove (or minimise) the scatter peaks from the acquired EEM data after collection. Several methods have been available to mitigate the effects of the Rayleigh and Raman scatter, such as weighting, subtraction of a standard, constraints in the PARAFAC decomposition, replacement of the scatter peaks with either interpolated values or insertion of missing or zero values. In this study, the interpolation way (on which interested readers are referred to; M. Bahram, R. Bro, C. Stedmon, A. Afkhami. Handling of Rayleigh and Raman scatter for PARAFAC modeling of fluorescence data using interpolation. *J. Chemom.* 2006, 20, 99-105) was employed to overcome the problem of Rayleigh scattering. It is beneficial to the subsequent data analysis.

The Penalty Parameter ($\lambda$) and Similarity Threshold

Two parameters, the penalty parameter $\lambda$, and the similarity threshold, are critical to the understanding of the SimI concept. There now follows a discussion of how to determine $\lambda$ as well as how to define the similarity threshold by both the EEM and TSFS data acquired from HPTS solutions.

TABLE 1A

Case study 2: concentrations of HPTS solutions and the resulting similarity values obtained from the individual EEM data with different penalty parameter $\lambda$.

| | | SimI values obtained from EEM data (SimI_eem) | | | | | | | |
|---|---|---|---|---|---|---|---|---|---|
| No. | Conc. (M) | $\lambda = 0.5$ | $\lambda = 1.0$ | $\lambda = 2.0$ | $\lambda = 3.0$ | $\lambda = 4.0$ | $\lambda = 5.0$ | $\lambda = 6.0$ | $\lambda = 8.0$ |
| 1  | 0.0 | 0.5048 | 0.0096 | −0.9809 | −1.9713 | −2.9618 | −3.9522 | −4.9426 | −6.9235 |
| 2  | $0.50 \times 10^{-7}$ | 0.5490 | 0.0980 | −0.8041 | −1.7061 | −2.6082 | −3.5102 | −4.4123 | −6.2164 |
| 3  | $1.25 \times 10^{-7}$ | 0.5918 | 0.1837 | −0.6327 | −1.4490 | −2.2653 | −3.0816 | −3.8980 | −5.5306 |
| 4  | $2.50 \times 10^{-7}$ | 0.6599 | 0.3197 | −0.3606 | −1.0409 | −1.7212 | −2.4015 | −3.0818 | −4.4424 |
| 5  | $5.00 \times 10^{-7}$ | 0.7631 | 0.5262 | 0.0524 | −0.4214 | −0.8952 | −1.3690 | −1.8427 | −2.7903 |
| 6  | $1.25 \times 10^{-6}$ | 0.9758 | 0.9516 | 0.9032 | 0.8548 | 0.8064 | 0.7580 | 0.7097 | 0.6129 |
| 7  | $1.375 \times 10^{-6}$ | 1.0000 | 1.0000 | 1.0000 | 1.0000 | 1.0000 | 1.0000 | 1.0000 | 1.0000 |
| 8  | $1.500 \times 10^{-6}$ | 0.9799 | 0.9599 | 0.9197 | 0.8796 | 0.8395 | 0.7993 | 0.7592 | 0.6789 |
| 9  | $2.00 \times 10^{-6}$ | 0.9083 | 0.8165 | 0.6330 | 0.4495 | 0.2660 | 0.0825 | −0.1010 | −0.4679 |
| 10 | $2.215 \times 10^{-6}$ | 0.8935 | 0.7870 | 0.5740 | 0.3610 | 0.1480 | −0.0649 | −0.2779 | −0.7039 |
| 11 | $1.375 \times 10^{-6}$ | 0.9951 | 0.9902 | 0.9804 | 0.9706 | 0.9608 | 0.9510 | 0.9412 | 0.9216 |

Sample 11 corresponds to the HPTS working solution in Case study 1.

Table 1A Case study 2: concentrations of HPTS solutions and the resulting similarity values obtained from the individual EEM data with different penalty parameter $\lambda$. Sample 11 corresponds to the HPTS working solution in Case study 1.

Under eight penalty levels of $\lambda=0.5, 1.0, 2.0, 3.0, 4.0, 5.0, 6.0$ and $8.0$, the EEM and TSFS data of the HPTS solutions in Case study 2 were tested for SimI performance. All the SimI values were calculated by referencing No7 (viz. $1.375 \times 10^{-6}$ M HPTS solution). The results are tabulated in Tables 1A-1B, from which one can observe that:

1) A small $\lambda$ value cannot adequately distinguish the variation from samples with small yet significant concentration differences. For example, the SimI performs poorly on the EEM and TSFS data when $\lambda \leq 3$. It fails to clearly identify a significant, yet small concentration difference of approximately 9% between the reference sample (No7) and the No6 and No8 HPTS solution samples. In these cases, the corresponding SimI values are close to 1.0.

2) A large $\lambda$ value can overly magnify the small variation originating from the inevitable instrumentation noise or intrinsic experimental conditions. For example in the case of fluorescence datasets, when $k \geq 5$, sample No11 (HPTS working solution) shows up as being very different from the No7 reference sample (see the resulting SimI_eem and SimI$_{13}$ tsfs values). As a consequence, such an over-magnified variation would be mistaken for a significant difference owing to sample inherency. This indicates that the value of $\lambda$ is too large to evaluate this type of EEM/TSFS data correctly. In fact, it is the experimental tolerance that caused the HPTS working solution to be a little different than the reference concerning their concentrations and the resulting similarity values.

For this type of sample class, a penalty parameter value of $\lambda=4$ is found to appropriately assess the variations of samples in terms of their spectroscopic intensities which are directly related to small, yet significant changes in concentration of the fluorescent species. The SimI values obtained from both the EEM and TSFS data are acceptable for accurate qualitative and quantitative analysis.

TABLE 1B

Case study 2: concentrations of HPTS solutions of samples and the resulting similarity values obtained from the individual TSFS data with different penalty parameter $\lambda$.

| | | SimI values obtained from TSFS data (SimI_tsfs) | | | | | | | |
|---|---|---|---|---|---|---|---|---|---|
| No. | Conc. (M) | $\lambda = 0.5$ | $\lambda = 1.0$ | $\lambda = 2.0$ | $\lambda = 3.0$ | $\lambda = 4.0$ | $\lambda = 5.0$ | $\lambda = 6.0$ | $\lambda = 8.0$ |
| 1  | 0.0 | 0.5037 | 0.0073 | −0.9854 | −1.9781 | −2.9707 | −3.9634 | −4.9561 | −6.9415 |
| 2  | $0.50 \times 10^{-7}$ | 0.5400 | 0.0800 | −0.8400 | −1.7600 | −2.6800 | −3.6000 | −4.5200 | −6.3600 |
| 3  | $1.25 \times 10^{-7}$ | 0.5813 | 0.1626 | −0.6748 | −1.5122 | −2.3496 | −3.1870 | −4.0244 | −5.6991 |
| 4  | $2.50 \times 10^{-7}$ | 0.6497 | 0.2995 | −0.4011 | −1.1016 | −1.8021 | −2.5027 | −3.2032 | −4.6042 |
| 5  | $5.00 \times 10^{-7}$ | 0.7545 | 0.5090 | 0.0180 | −0.4730 | −0.9641 | −1.4551 | −1.9461 | −2.9281 |
| 6  | $1.25 \times 10^{-6}$ | 0.9755 | 0.9510 | 0.9020 | 0.8530 | 0.8039 | 0.7549 | 0.7059 | 0.6079 |
| 7  | $1.375 \times 10^{-6}$ | 1.0000 | 1.0000 | 1.0000 | 1.0000 | 1.0000 | 1.0000 | 1.0000 | 1.0000 |
| 8  | $1.50 \times 10^{-6}$ | 0.9785 | 0.9571 | 0.9141 | 0.8712 | 0.8282 | 0.7853 | 0.7423 | 0.6564 |
| 9  | $2.00 \times 10^{-6}$ | 0.9054 | 0.8107 | 0.6214 | 0.4321 | 0.2428 | 0.0535 | −0.1358 | −0.5144 |
| 10 | $2.215 \times 10^{-6}$ | 0.8892 | 0.7784 | 0.5568 | 0.3352 | 0.1137 | −0.1079 | −0.3295 | −0.7727 |
| 11 | $1.375 \times 10^{-6}$ | 0.9957 | 0.9913 | 0.9827 | 0.9740 | 0.9654 | 0.9567 | 0.9481 | 0.9308 |

Sample 11 corresponds to the HPTS working solution in Case study 1.

Table 1B Case study 2: concentrations of HPTS solutions of samples and the resulting similarity values obtained from the individual TSFS data with different penalty parameter $\lambda$. Sample 11 corresponds to the HPTS working solution in Case study 1.

In Case study 1, a reference spectrum was first acquired by the median operation upon forty-five measurements (using spectra that had been corrected for Rayleigh scattering of the EEM spectra) which excluded measurements from 4 samples (HPTS30-33). Then, with $\lambda=4$, the SimI values were calculated for all the forty-nine sample measurements against the pre-acquired reference, as summarized in Table 2.

It can be found that the samples HPTS30-33 have lower SimI values (less than 0.90), and this indicates that they are significantly different. They are different because, they were stored under different environmental conditions for a number of days and the solutions absorbed carbon dioxide from the air, changing the pH from 7.6 to approximately 7.3. This caused a small change in the EEM spectral data which was easily uncovered by the SimI method.

In the case of TSFS data, $\lambda=4$ was used for the SimI calculation and the results are listed in Table 2. The results agree very well with the SimI_eem results and the similarity values (i.e., Simi_tsfs) of HPTS30-33 are far smaller, less than 0.85, whilst the SimI values of the remaining measurements are all close to one.

TABLE 2

Forty-nine measurements of HPTS working solution and their resulting SimI values obtained with $\lambda = 4.0$ from the individual EEM and TSFS data.

| No. | Sample ID | SimI_eem | SimI_tsfs |
|---|---|---|---|
| 1 | HPTS01 | 0.9614 | 0.9484 |
| 2 | HPTS02 | 0.9830 | 0.9838 |
| 3 | HPTS03 | 0.9866 | 0.9862 |
| 4 | HPTS04 | 0.9851 | 0.9873 |
| 5 | HPTS05 | 0.9836 | 0.9839 |
| 6 | HPTS06 | 0.9846 | 0.9846 |
| 7 | HPTS07 | 0.9815 | 0.9715 |
| 8 | HPTS08 | 0.9812 | 0.9738 |
| 9 | HPTS09 | 0.9838 | 0.9867 |
| 10 | HPTS10 | 0.9860 | 0.9848 |
| 11 | HPTS11 | 0.9776 | 0.9741 |
| 12 | HPTS12 | 0.9815 | 0.9817 |
| 13 | HPTS13 | 0.9740 | 0.9784 |
| 14 | HPTS14 | 0.9870 | 0.9800 |
| 15 | HPTS15 | 0.9783 | 0.9779 |
| 16 | HPTS16 | 0.9893 | 0.9899 |
| 17 | HPTS17 | 0.9918 | 0.9879 |
| 18 | HPTS18 | 0.9890 | 0.9835 |
| 19 | HPTS19 | 0.9775 | 0.9663 |
| 20 | HPTS20 | 0.9909 | 0.9873 |
| 21 | HPTS21 | 0.9788 | 0.9708 |
| 22 | HPTS22 | 0.9825 | 0.9712 |
| 23 | HPTS23 | 0.9801 | 0.9802 |
| 24 | HPTS24 | 0.9787 | 0.9743 |
| 25 | HPTS25 | 0.9812 | 0.9722 |
| 26 | HPTS26 | 0.9746 | 0.9703 |
| 27 | HPTS27 | 0.9859 | 0.9816 |
| 28 | HPTS28 | 0.9777 | 0.9772 |
| 29 | HPTS29 | 0.9837 | 0.9809 |
| 30 | HPTS30 | 0.8942 | 0.8347 |
| 31 | HPTS31 | 0.8984 | 0.8447 |
| 32 | HPTS32 | 0.8951 | 0.8388 |
| 33 | HPTS33 | 0.8984 | 0.8460 |
| 34 | HPTS34 | 0.9760 | 0.9766 |
| 35 | HPTS35 | 0.9913 | 0.9914 |
| 36 | HPTS36 | 0.9926 | 0.9865 |
| 37 | HPTS37 | 0.9916 | 0.9878 |
| 38 | HPTS38 | 0.9906 | 0.9872 |
| 39 | HPTS39 | 0.9732 | 0.9715 |
| 40 | HPTS40 | 0.9723 | 0.9717 |
| 41 | HPTS41 | 0.9798 | 0.9655 |
| 42 | HPTS42 | 0.9819 | 0.9715 |
| 43 | HPTS43 | 0.9844 | 0.9767 |
| 44 | HPTS44 | 0.9861 | 0.9940 |
| 45 | HPTS45 | 0.9863 | 0.9858 |
| 46 | HPTS46 | 0.9880 | 0.9848 |
| 47 | HPTS47 | 0.9864 | 0.9912 |
| 48 | HPTS48 | 0.9901 | 0.9868 |
| 49 | HPTS49 | 0.9800 | 0.9777 |

From a statistical viewpoint, suppose that both the above obtained SimI_eem and SimI_tsfs values follow t-distribution individually, all the forty-nine measurements of HPTS solutions were then tested with a confidence level of $\alpha=0.05$. The HPTS30~33 locate outside the 95% confidence limit, and they are identified as significant outliers. In conclusion, case studies 1 and 2 indicate that a penalty parameter $\lambda=4$ is able to provide satisfactory SimI performance for the analysis of samples using multidimensional fluorescence measurements which can identify sample small variations due to concentration changes rather than instrumental noise.

Figure 2A:
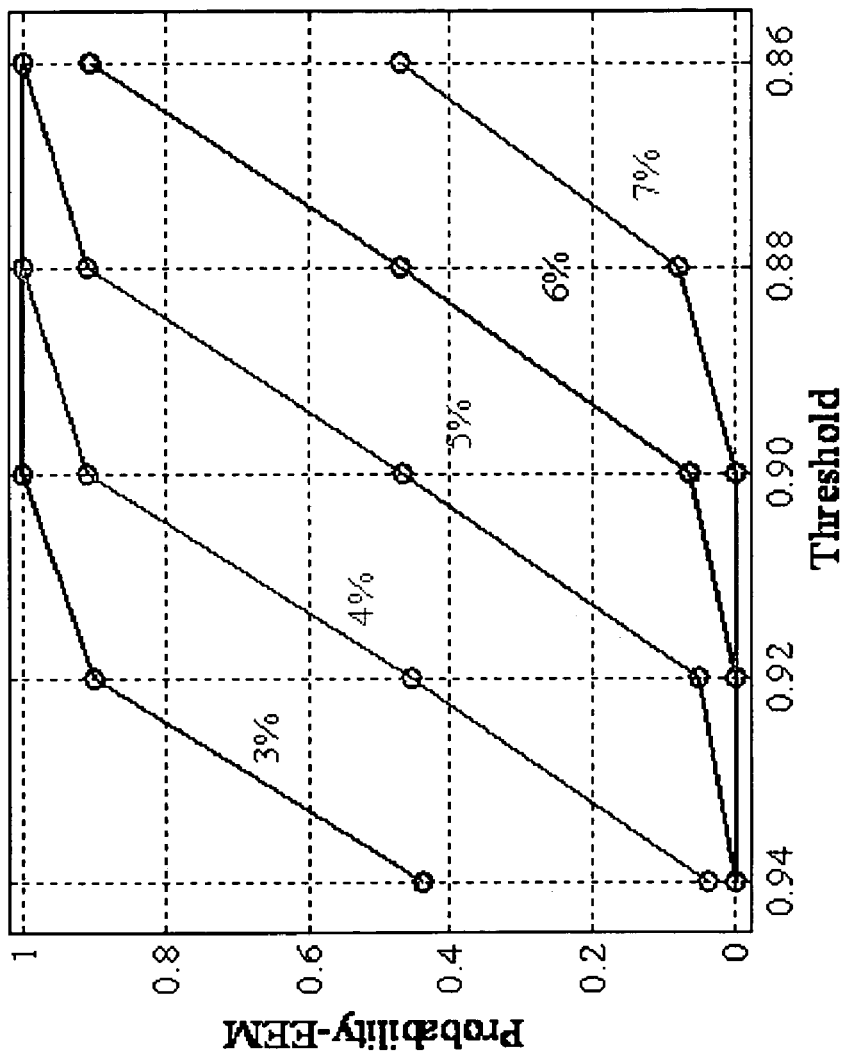
FIGS. 2A-2B show the probabilities for the similarity threshold for the performance of the SimI method of the present invention in Case study 3 from the simulated EEM data (2A), and from the simulated TSFS data (2B).
Figure 2B:
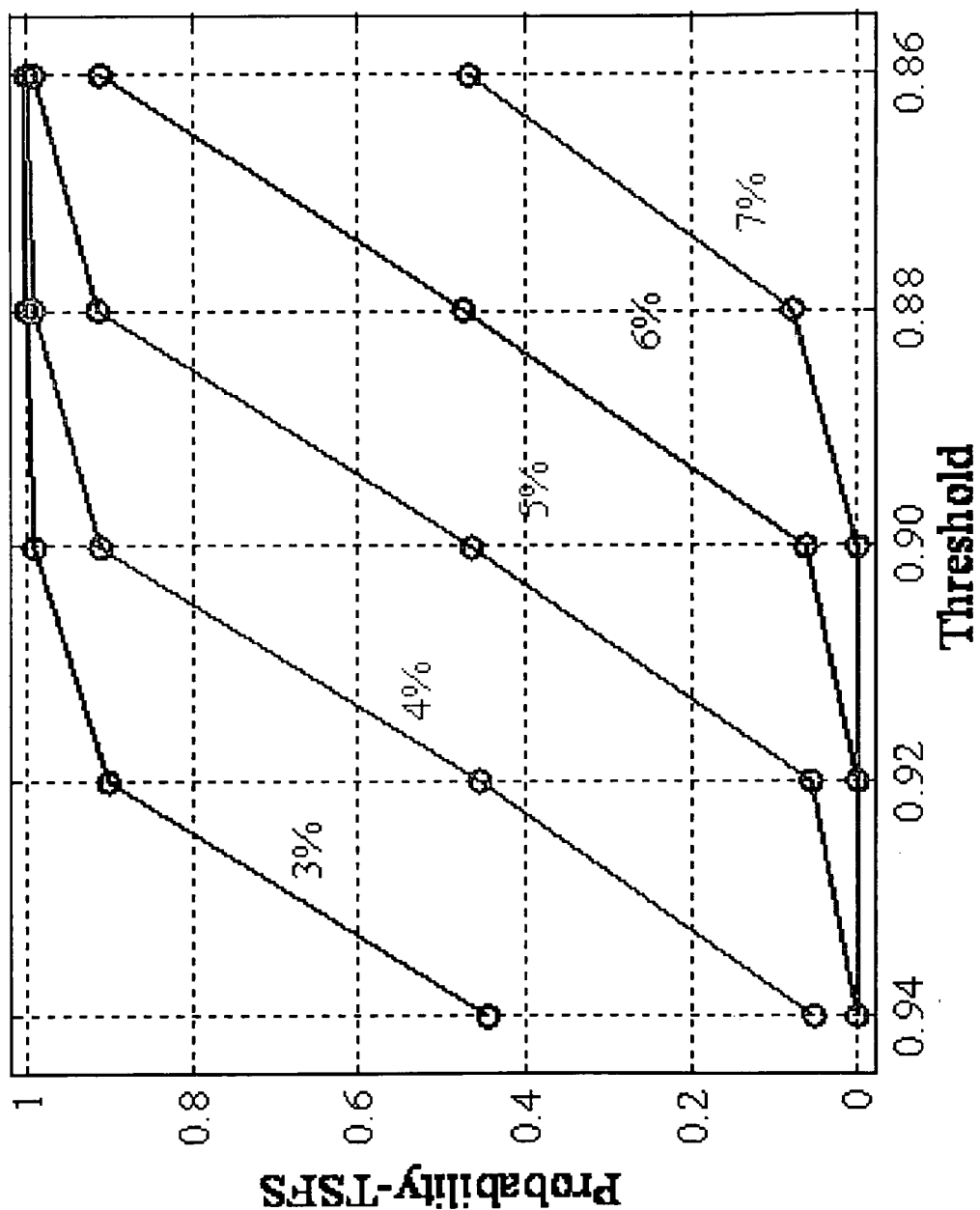
Figure 3A:
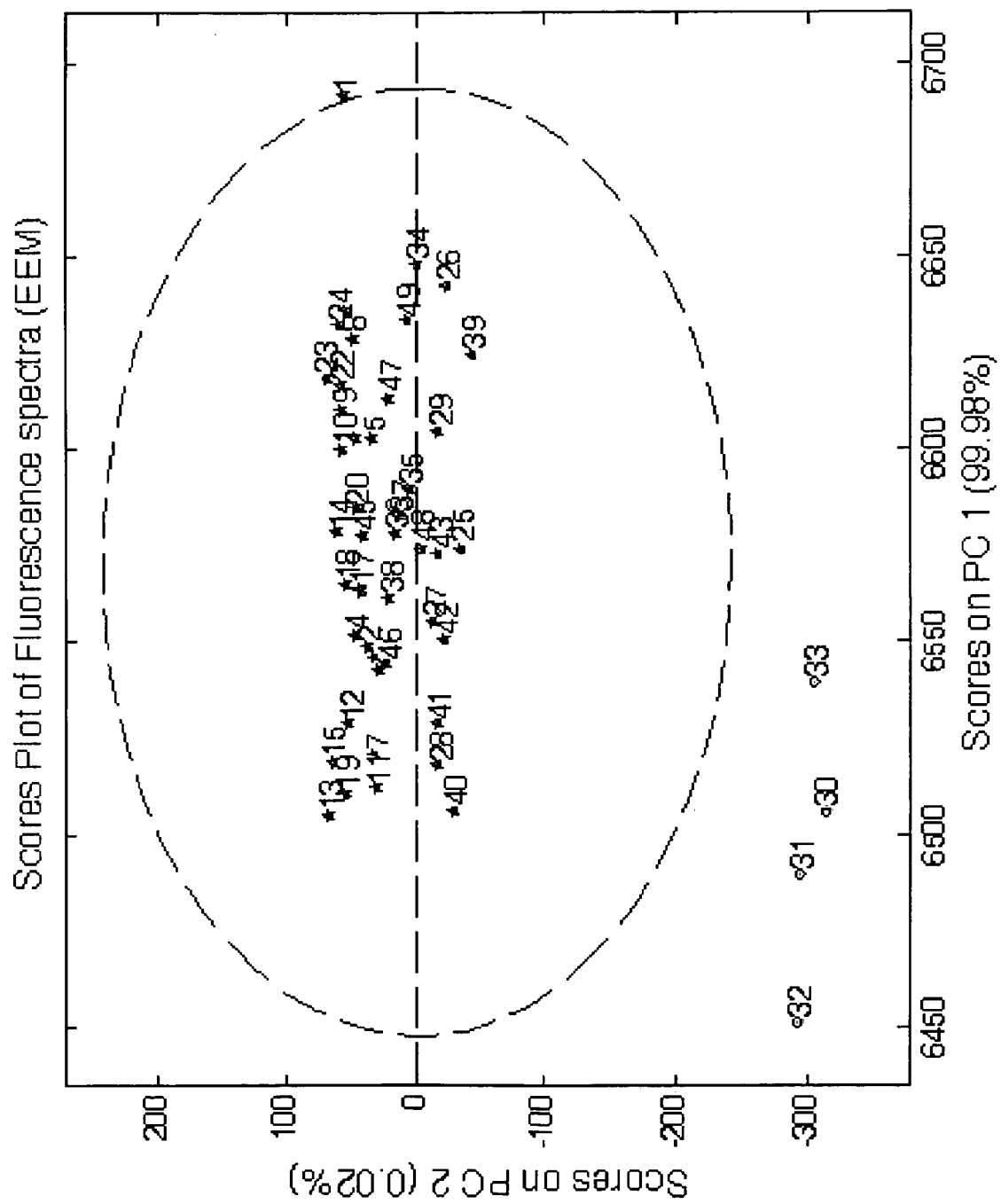
FIGS. 3A-3D depict PC scores and $T^2$ statistic plots of forty-nine HPTS measurements over thirteen days obtained by MPCA from fluorescence EEMs and TSFS data. The first two PCs and significant level $\alpha=0.05$ were used to calculate the $T^2_\alpha$ and $T^2$.
Figure 3B:
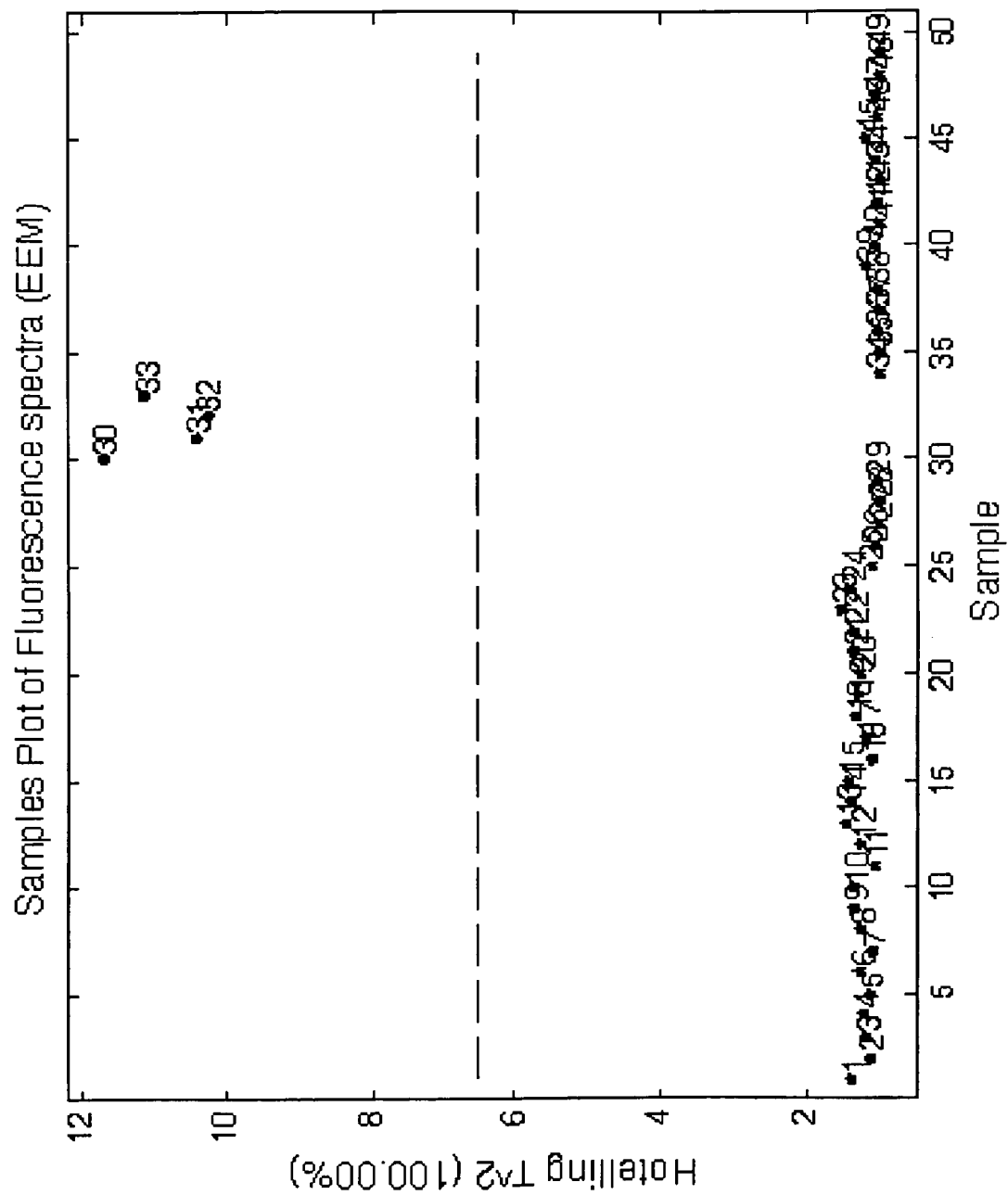
Figure 3C:
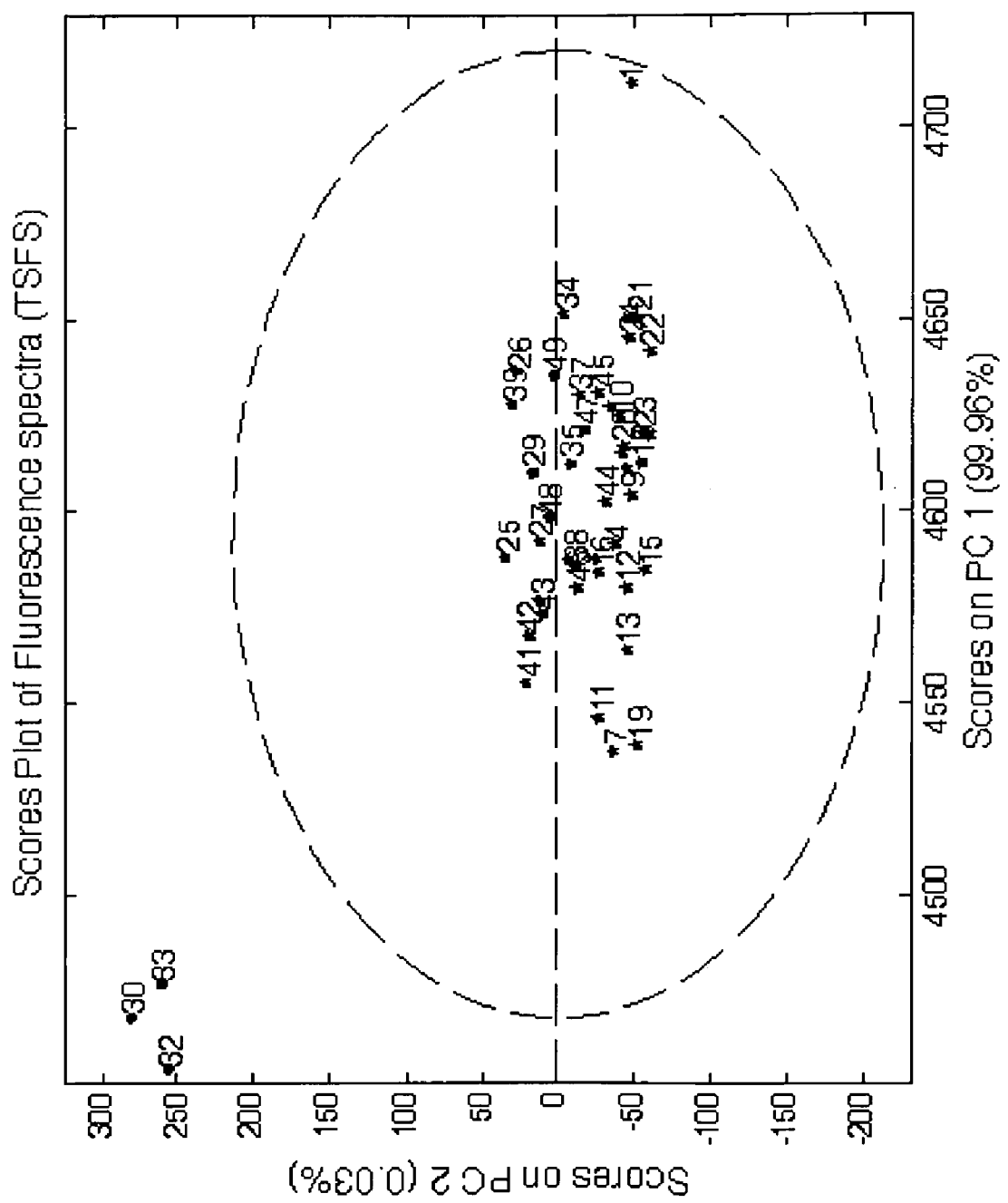
Figure 3D:
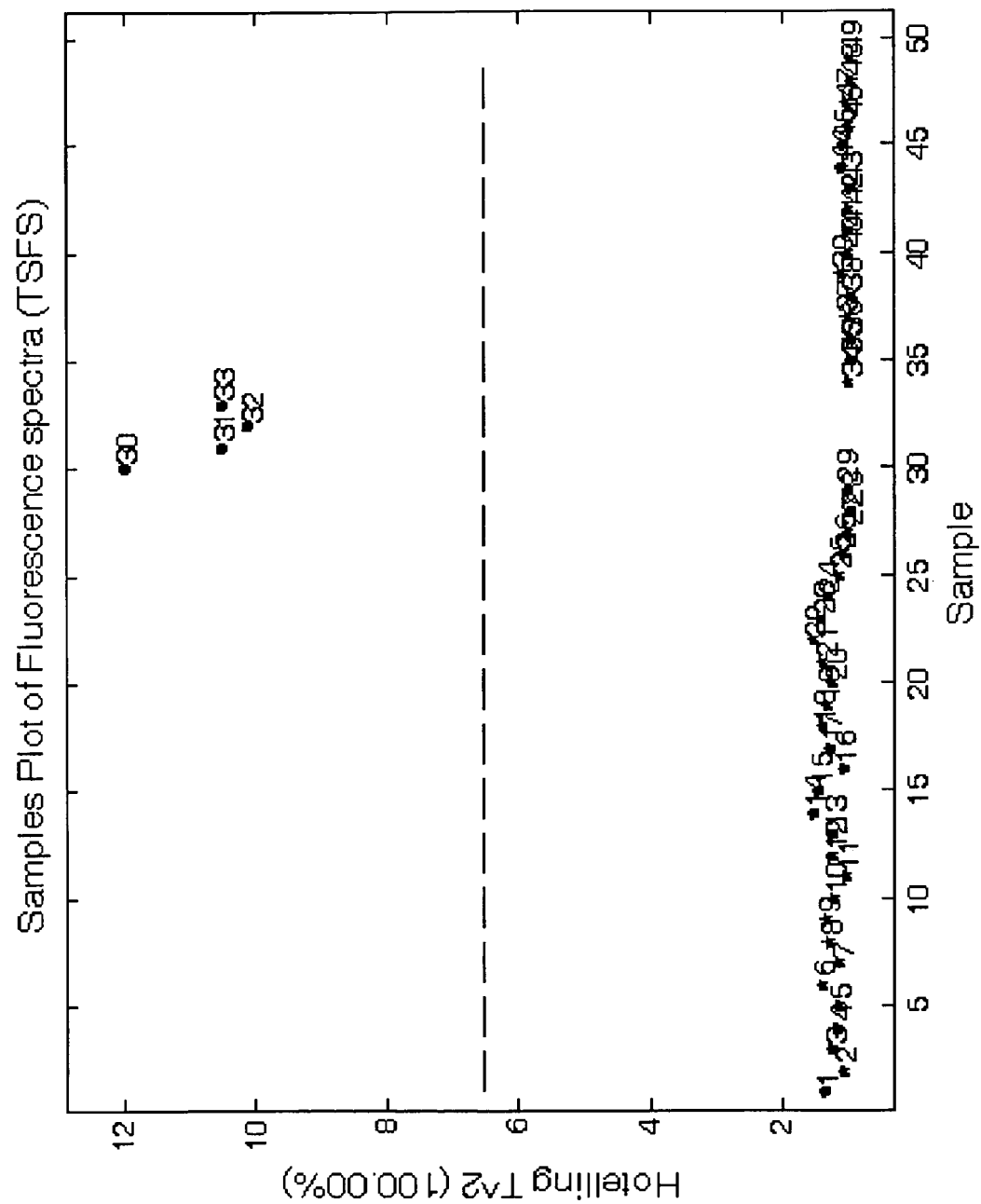

To define a proper similarity threshold for the SimI method, five simulation scenarios (Case study 3) were explored respectively. For each scenario, all the SimI values of 1800 simulated EEM and TSFS data against their individual references were calculated. Afterwards, the probabilities that the resulting SimI values are larger than five possible predetermined similarity thresholds (viz. 0.94, 0.92, 0.90, 0.88, and 0.86) were computed and compared. All the results obtained from the five simulation scenarios are presented in Table 3, and in FIGS. 2A-2B to graphically facilitate i) the extraction of general trends of similarity thresholds and ii) the insight capability of the SimI regarding its performance to detect sample variations with these similarity thresholds. One can observe that the probability of the SimI values above a nominated threshold decreases when the variations imposed to the simulated EEM/TSFS data become larger and larger. The same trend occurs to all the cases (i.e., five simulation scenarios by five similarity thresholds). Particular attention should be given to that if $\lambda=4$ and threshold=0.90 the probabilities are 0.47 and 0.46 respectively for the EEM and TSFS data. This significantly infers that the similarity threshold of 0.90 enables the SimI to identify around 5% variation of sample in terms of either spectral intensity or compositional concentration.

TABLE 3

Probabilities of the resulting SimI values of the simulated data in five simulation scenarios, computed with five similarity thresholds and $\lambda = 4.0$.

| | Probability | | | | | | | | | |
|---|---|---|---|---|---|---|---|---|---|---|
| | SimI_eem | | | | | SimI_tsfs | | | | |
| | Threshold | | | | | | | | | |
| Variation | 0.94 | 0.92 | 0.90 | 0.88 | 0.86 | 0.94 | 0.92 | 0.90 | 0.88 | 0.86 |
| 3.0% | 0.44 | 0.90 | 1.00 | 1.00 | 1.00 | 0.44 | 0.90 | 0.99 | 1.00 | 1.00 |
| 4.0% | 0.04 | 0.45 | 0.91 | 1.00 | 1.00 | 0.05 | 0.45 | 0.91 | 0.99 | 1.00 |
| 5.0% | 0.00 | 0.05 | 0.47 | 0.91 | 1.00 | 0.00 | 0.06 | 0.46 | 0.91 | 0.99 |

TABLE 3-continued

Probabilities of the resulting SimI values of the simulated data in five simulation scenarios, computed with five similarity thresholds and $\lambda = 4.0$.

| | Probability | | | | | | | | | |
|---|---|---|---|---|---|---|---|---|---|---|
| | SimI_eem | | | | | SimI_tsfs | | | | |
| | Threshold | | | | | | | | | |
| Variation | 0.94 | 0.92 | 0.90 | 0.88 | 0.86 | 0.94 | 0.92 | 0.90 | 0.88 | 0.86 |
| 6.0% | 0.00 | 0.00 | 0.07 | 0.47 | 0.91 | 0.00 | 0.00 | 0.06 | 0.47 | 0.91 |
| 7.0% | 0.00 | 0.00 | 0.00 | 0.08 | 0.47 | 0.00 | 0.00 | 0.00 | 0.08 | 0.47 |

The fluorescence measurements of HPTS solutions illustrated in Case study 1 and 2 have also greatly proven this point, and the similarity threshold of 0.90 is thereby decided for the SimI in this study. Of course, too small threshold will not provide enough good detection ability to the SimI model. One can define different similarity threshold and penalty parameter when the SimI method is used for evaluating the variability of samples by means of their multidimensional fluorescence data, which depend on how strictly they are evaluated in practice. The relationship amongst the similarity threshold, the penalty parameter $\lambda$ and the detection limit of variation (var) can be generalized approximately, $$\text{Threshold} = 1 - \lambda \frac{\text{var}}{2 \pm \text{var}} \quad (14)$$

Similarity Index Versus Matrix Congruence Coefficient

Despite being mutually different in meaning, the MatrixCC and SimI may be regarded as the degree of association between two topographies of data or multiple independent variables. There a numerical example discusses the applicability of the MatrixCC and SimI, either as a way to infer correlation, or to test linearity, of actual fluorescence measurements of HPTS solutions in Case study 2.

tral intensity and compositional concentration. The magnitudes of the SimI values rely on the concentration variation (which affects the fluorescence intensity) of the samples from the reference No7.

As the concentration of the HPTS sample solutions deviates from the reference sample, the SimI values acquired from both the EEM and TSFS data become smaller. For example, samples No6 and No8, have SimI values of 0.81 and 0.84 for the EEM spectra, and 0.80 and 0.83 for the TSFS data, respectively. Therefore, an approximate 9% concentration difference between the samples and reference was successfully quantitatively discriminated by the SimI method. However, the MatrixCC simply determines whether the spectral intensities of samples vary in linearity regardless of to what degree the variations of compositional concentration occur. Except No1 (of pure water) and No2 (with super low compositional concentration), all the HPTS solutions give very high MatrixCC values, nearly equal to one. This is because the MatrixCC measures the linear correlation between two multidimensional objects, behaving insensitively in the MatrixCC value.

Similarity Index Versus Multiway Principal Component Analysis

MPCA was carried out on the unfolded EEM and TSFS data of the forty-nine HPTS measurements in Case study 1. There developed two MPCA models individually with two PCs, which both capture 100% of the variance contained in

TABLE 4

The concentrations of HPTS solutions and the resulting similarity values obtained from the individual EEM and TSFS data for the comparison of the SimI where $\lambda = 4.0$ with the MatrixCC.

| No. | Conc. (M) | SimI_eem | MatrixCC_eem | SimI_tsfs | MatrixCC_tsfs |
|---|---|---|---|---|---|
| 1 | 0.00 | −2.9618 | 0.2594 | −2.9707 | 0.1319 |
| 2 | $0.50 \times 10^{-7}$ | −2.6082 | 0.9259 | −2.6800 | 0.8791 |
| 3 | $1.25 \times 10^{-7}$ | −2.2653 | 0.9751 | −2.3496 | 0.9641 |
| 4 | $2.50 \times 10^{-7}$ | −1.7212 | 0.9943 | −1.8021 | 0.9917 |
| 5 | $5.00 \times 10^{-7}$ | −0.8952 | 0.9983 | −0.9641 | 0.9976 |
| 6 | $1.25 \times 10^{-6}$ | 0.8064 | 1.0000 | 0.8039 | 1.0000 |
| 7 | $1.375 \times 10^{-6}$ | 1.0000 | 1.0000 | 1.0000 | 1.0000 |
| 8 | $1.50 \times 10^{-6}$ | 0.8395 | 0.9999 | 0.8282 | 1.0000 |
| 9 | $2.00 \times 10^{-6}$ | 0.2660 | 0.9998 | 0.2428 | 0.9998 |
| 10 | $2.215 \times 10^{-6}$ | 0.1480 | 0.9997 | 0.1137 | 0.9997 |

According to Eqs (1) and (11), referencing No7 the similarity values of the ten solutions were calculated by the SimI and MatrixCC methods based on the EEM and TSFS data, respectively. The results are presented in Table 4. The SimI discloses how the solutions differ from the reference in specthe data. Table 5 details the variance captured by each PC and also the cumulative variance captured. FIGS. 3A-3D display the scatter plots of the scores together with the confidence ellipses at the significance level of $\alpha = 0.05$ and the $T^2$ statistics obtained therefrom.

TABLE 5

Variance captured by the MPCA models on the EEM and TSFS
data of forty-nine HPTS measurements in Case study 1.

| PC | % Variance captured (EEM) | | % Variance captured (TSFS) | |
|---|---|---|---|---|
| | This PC | Total | This PC | Total |
| 1 | 99.98 | 99.98 | 99.96 | 99.96 |
| 2 | 0.02 | 100.00 | 0.03 | 100.00 |

From the results, it is clear that,
1) The four measurements of HPTS30~33 are outside the 95% confidence limit for the scores plot, and they have higher $T^2$ statistics. These four measurements significantly differ from the remaining samples.
2) Except for HPTS30~33 the HPTS measurements exhibit similar values of their scores and $T^2$ statistics. A large percentage of explained variance reveals that the variability among them is captured by the MPCA model. Their variations within the model do not exceed the 95% confidence limit.
3) The EEM and TSFS data lead to almost identical MPCA results, and enable the identification of abnormal variations. MPCA and the SimI method coincide very well in performance.

To interpret the consistency of the MPCA results from the EEM and TSFS data, one can speculate that the TSFS data is possibly converted from a partial EEM spectrum, vice versa. An EEM spectrum looks like,

```
Excitation wavelengths                          A B C D E F G H I J
                                              A B C D E F G H I J
                                            A B C D E F G H I J
                                          A B C D E F G H I J
                                        A B C D E F G H I J
                                      A B C D E F G H I J
                                    A B C D E F G H I J
                                  A B C D E F G H I J
                                A B C D E F G H I J
                              A B C D E F G H I J
                                      Emission wavelengths
```

"A" means 1Δ difference between excitation and emission wavelengths, i.e., 1Δ=(Em-Ex), "B" means 2Δ difference, "C" means 3Δ difference, and so on.

Thus, the TSFS spectrum will be something like that after shifting the excitation row of the EEM,

```
Excitation wavelengths   A B C D E F G H I J
                         A B C D E F G H I J
                         A B C D E F G H I J
                         A B C D E F G H I J
                         A B C D E F G H I J
                         A B C D E F G H I J
                         A B C D E F G H I J
                         A B C D E F G H I J
                         A B C D E F G H I J
                         A B C D E F G H I J
                              Delta wavelengths
```

Apparently, the upper and lower triangular-shape areas of the EEM spectrum are missing in the TSFS data. Our practice has demonstrated that a partial EEM spectrum as underlined can be converted to the TSFS data. The converted TSFS data are nearly identical to the real experimental TSFS data when it comes to the same instrumental parameters such as detector, slit and voltage used for the EEM and TSFS spectra taken. It is worth pointing out that the EEM spectrum contains more potential information than the TSFS spectrum.

By means of one simulation scenario (1800 simulated EEMs included) in Case study 3 as well as the HPTS measurements (49 EEMs) in Case study 1, the SimI and MPCA methods are compared with respect to their computation speed in terms of elapsed time. Twenty computations were run on the 1849 EEM spectra totally. On the average, it took 2.2 sec to execute the SimI calculation using a 2.8 GHz Pentium D Dell Optiplex PC with 1.0 GB RAM, and 150.2 sec for running a simplest MPCA with two PCs. It is obvious that the SimI calculation is very rapid, 68 times faster than the simplest MPCA model. This rapidity is the key advantage of the SimI method.

It is possible to conclude that the performance of the SimI method is at least as good as MPCA. The SimI method permits the evaluation of the resultant variance in the multidimensional fluorescence topographies from a large set of measurements with the purpose of the simplicity and rapidity on the operation. The output of the SimI gives a clear indication of abnormal variations that enables the identification of significant differences between samples.

Similarity Index Versus Parallel Factor Analysis

Figure 4A:
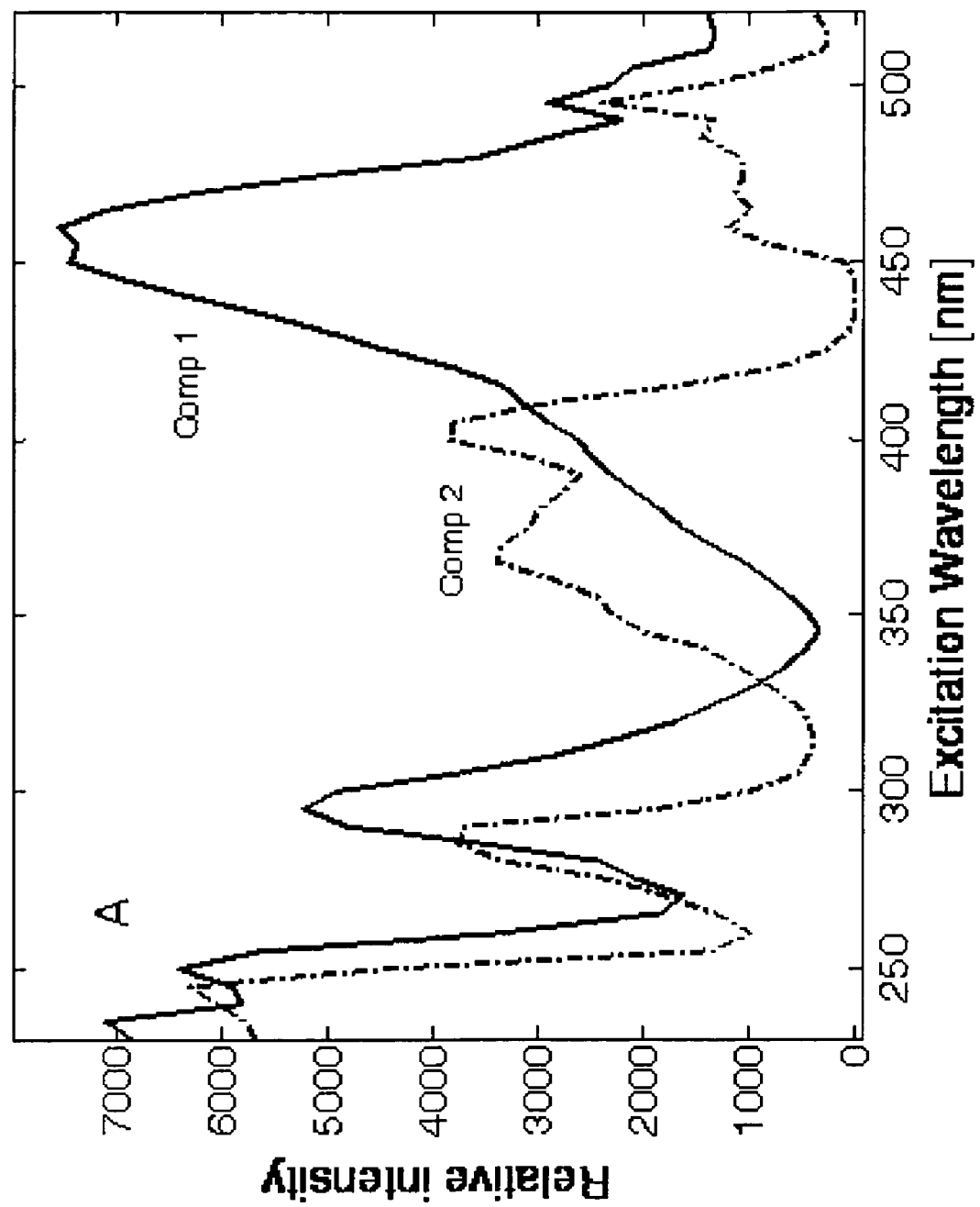
FIGS. 4A-4C illustrates relative spectral and concentration profiles of two components decomposed by PARAFAC model on the EEMs of the forty-nine measurements of HPTS solutions in Case study 1: (A) excitation spectral profiles, (B) emission spectral profiles, and (C) concentration profiles.
Figure 4B:
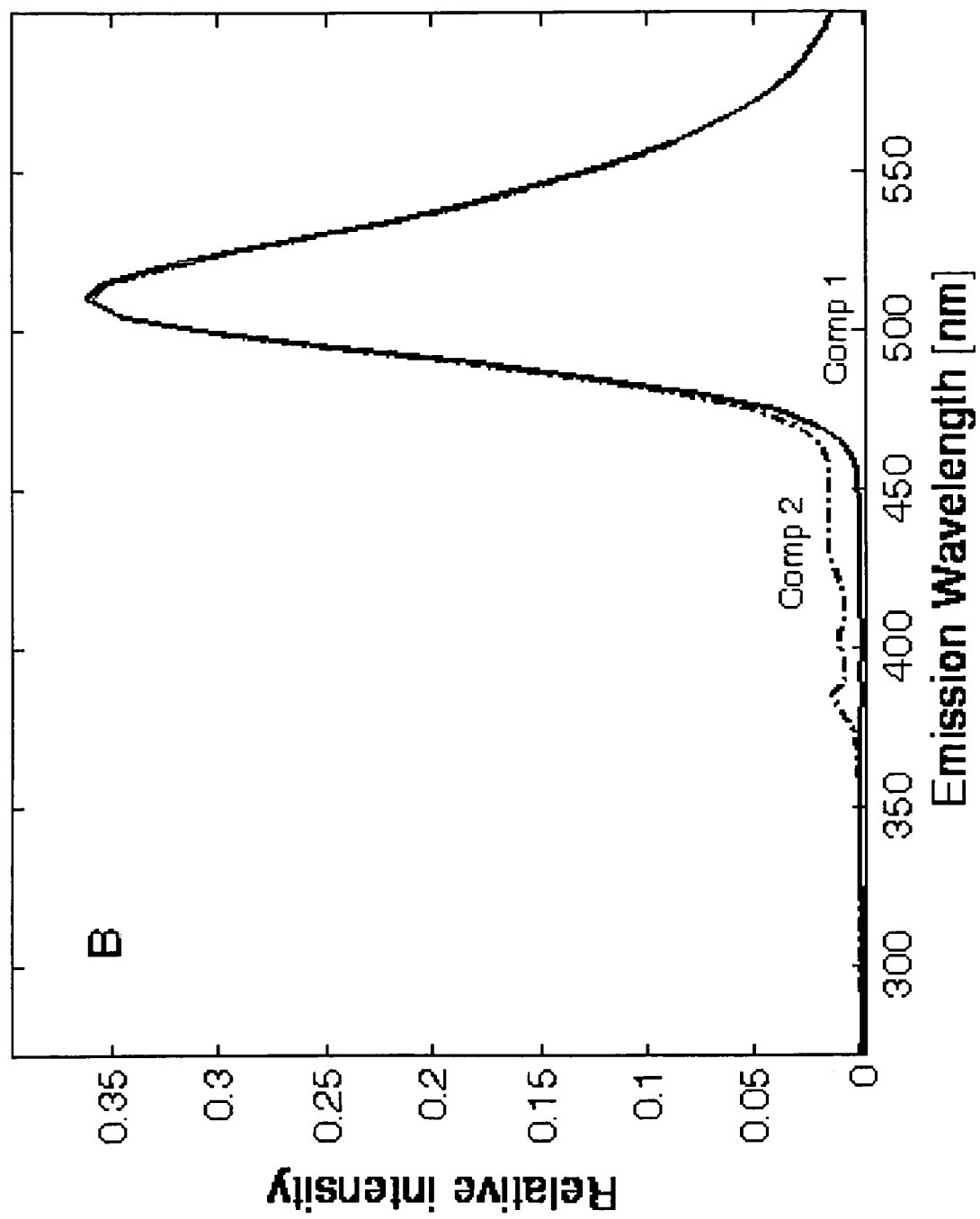
Figure 4C:
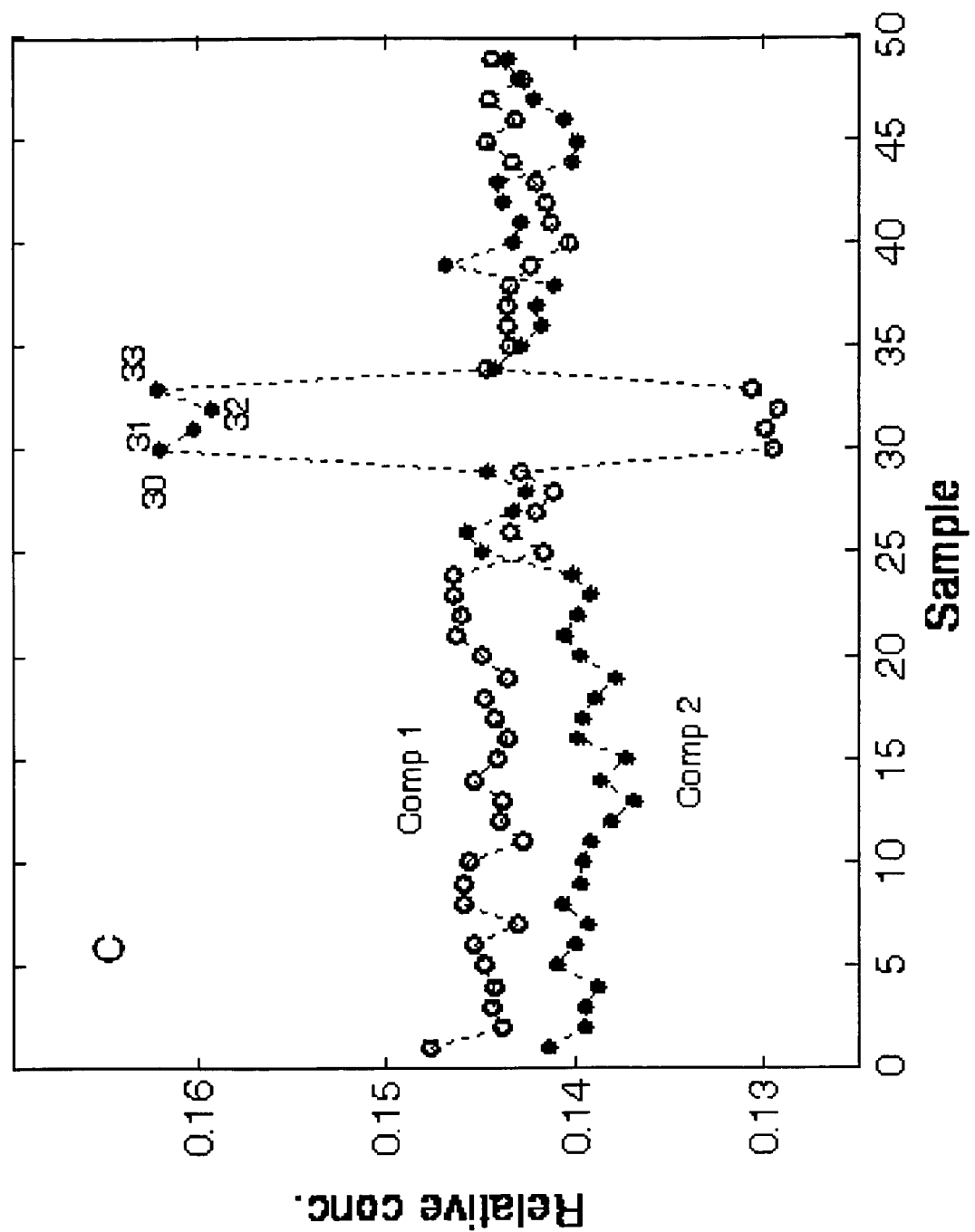

With the constraint of non-negativity, a PARAFAC model was built from the Rayleigh scattering-corrected EEM data of the forty-nine HPTS measurements in Case study 1. Based on the so-called core consistency diagnostic criterion, which involves observing the changes in the core consistency parameter as the number of trial components is increased, two components mainly contributing to the fluorescence spectra were determined for use. FIGS. 4A-4C delineate their estimated excitation (4A), emission spectrum (4B) and relative concentration profiles (4C). Clearly, such a fluorescence excitation-emission data set is validly visualized; Comp 1 and Comp 2 basically represent the compositions contained in the HPTS solution, and their contents are roughly stable or change gently during the experiment except the four measurements of HPTS30-33. The HPTS30-33 are significantly different from the remaining measurements in terms of the estimated concentrations of the two components, as are identified by the SimI model. However, it was not possible to execute the PARAFAC upon the preceding 1849 EEM spectra because the computation was so arduous and demanding in terms of computer memory. Provided that the PARAFAC is applied offline during model development phase, computation speed is still considered to be negligible.

A well-trained practitioner is required for valid data analysis using PARAFAC where manual intervention is required to properly determine the number of components and to logically interpret the model information produced. Furthermore, PARAFAC sometimes does not provide physically-interpretable information, and does not yield pure constituent profiles.

In comparison, the SimI method of the present invention allows for the rapid assessment of comparative complex aqueous samples without significant manual intervention.

Similarity Index Analysis of Aqueous Cell Culture Media

A practical application of SimI is demonstrated in Case study 4, a study of a dataset of 112 complex aqueous cell culture media samples. These media samples are all very closely related from a composition and chemical standpoint. There are several samples (which differ in age) from individual production lots sampled from an industrial bioprocess.

All the samples should be made to the same recipe and in theory should be identical, yielding identical spectra. However, in practice it is found that there are significant differences between samples originating from different lots. These samples all have very similar EEM and TSFS spectra, but there are significant differences in the spectra arising from small compositional changes. The objective was to rapidly discriminate the samples with significant spectral differences using the SimI method. These samples can then be studied in more detail to understand the lot-to-lot variability.

Figure 5A:
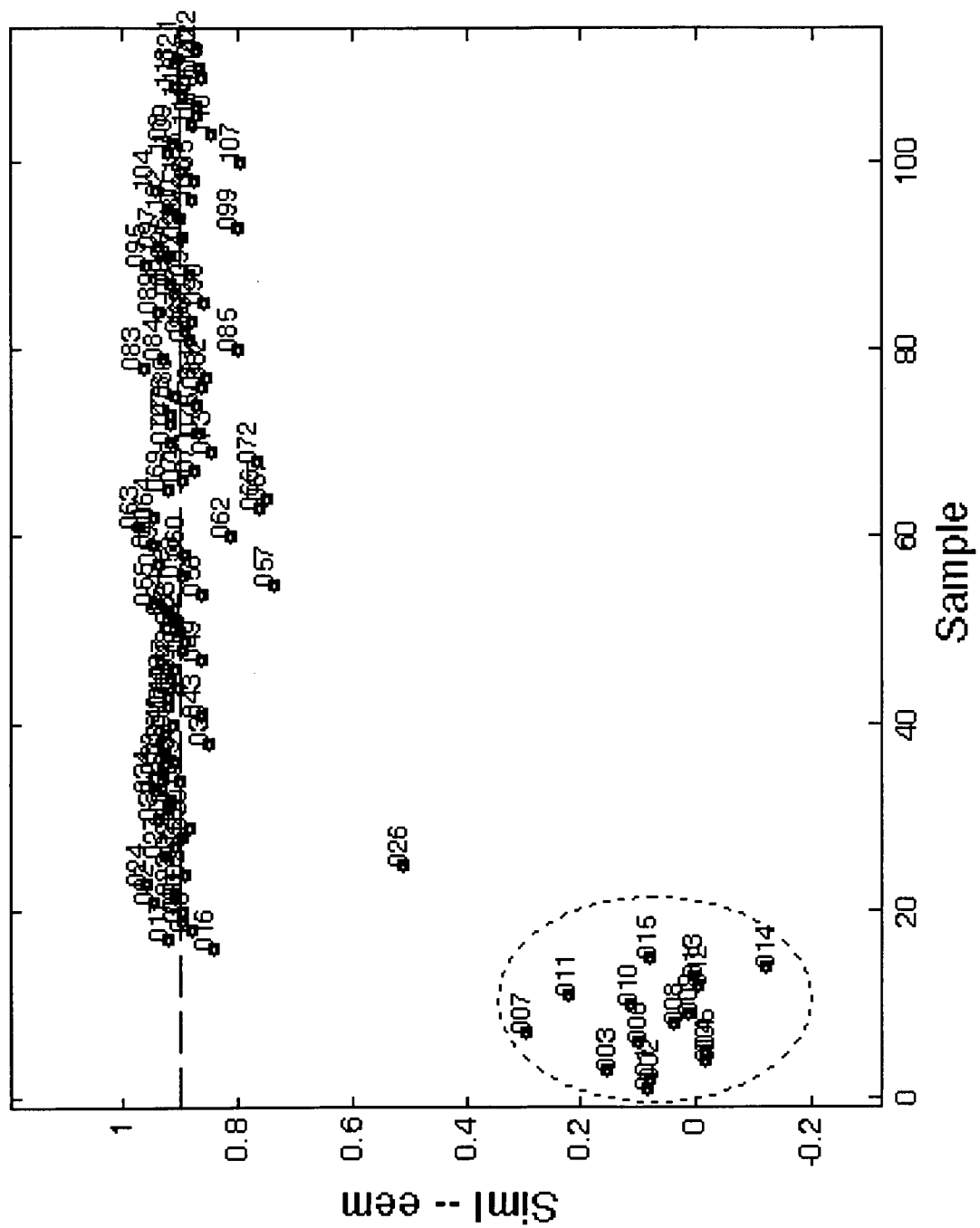
FIGS. 5A-5B show the SimI chart of the present invention for different 112 cell culture media obtained from the EEM and TSFS data.
Figure 5B:
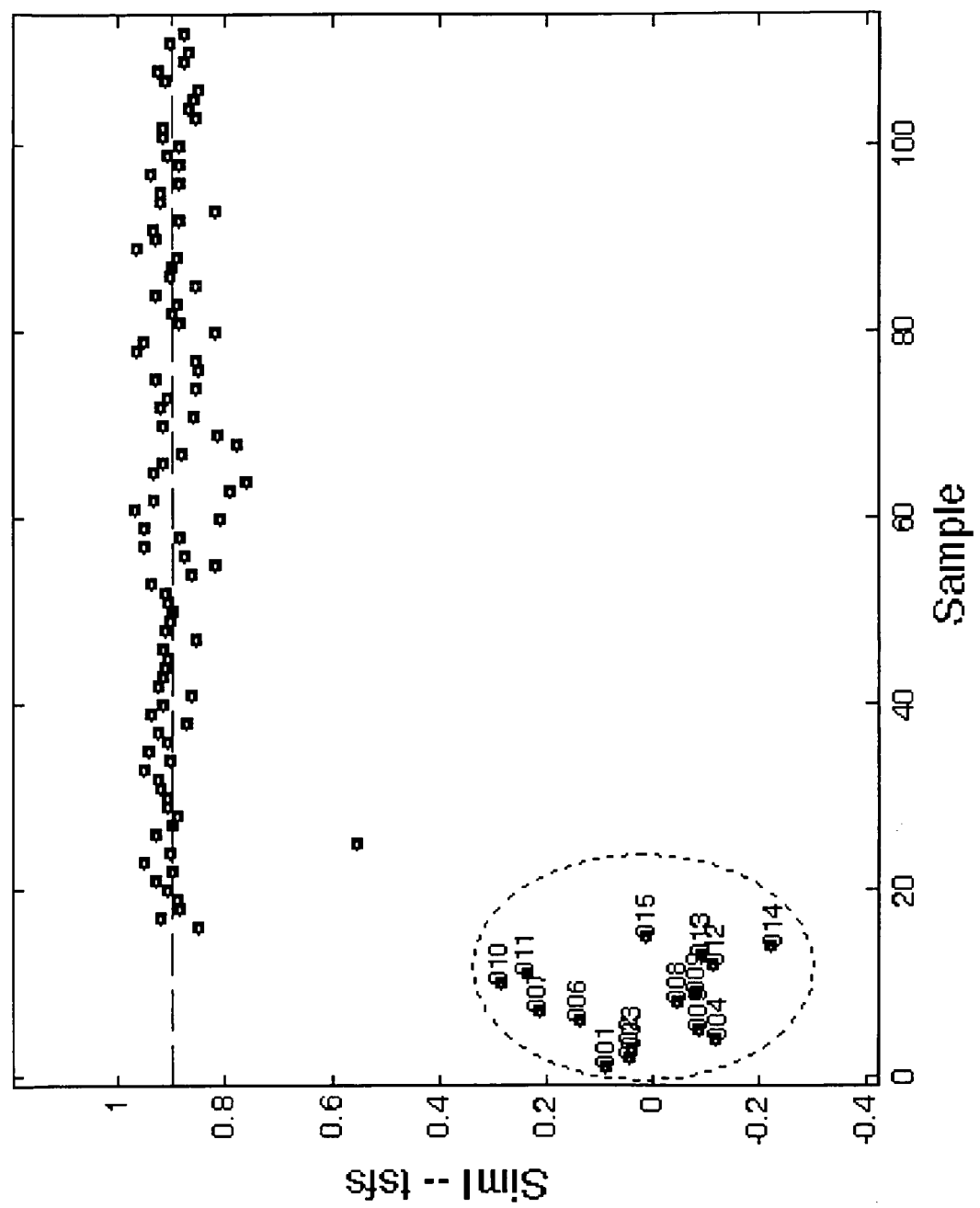

A reference spectrum was first extracted by a median operation from the Rayleigh scattering-corrected fluorescence EEMs of all the 112 samples. Then, the similarity values were calculated. The SimI results provide a basic level of quantitative information for a rapid assessment of similarity or dissimilarity between samples and the reference. The samples with low similarity values (the obvious outliers) were then left out (to minimize their leverage on the SimI model) and the remaining samples were used to build a new SimI model using a new reference spectrum and the SimI calculation was redone. FIGS. 5A-5B displays the similarity distribution of all 112 samples obtained from their EEM and TSFS spectra. A practical benefit of the SimI chart (like the $T^2$ statistic) is that it provides a useful numerical summary of sample variability and hence information on sample quality and consistency.

Based on the SimI results, the 001-015 samples are explicitly identified as significantly different (marked with an ellipsoid in FIGS. 5A-5B). Normal samples cluster around the specification threshold, indicating that they are very similar and their consistency quality is very good. A closer examination reveals that the 001-015 samples originated from a slightly different bioprocess, and it is the process variation that impacted the dissimilarity of these fifteen lots to the most normal lots representing a normal bioprocess. However, the 026 sample which is also far away from the normal samples is also identified as a significant outlier.

Case study 4 indicates that the SimI method is able to gauge the variability of complex aqueous cell culture media samples by using multidimensional fluorescence data in a relatively straightforward manner. The methodology and results can easily be generalized to an effective and potential solution for multivariate quality control of any complex aqueous based sample that is fluorescent. For example, in biopharmaceutical production where many different types of aqueous based materials are used in batches or continuous flow reactors, there is a need to measure and quantify the inevitable lot-to-lot variations arising from variation in raw materials quality, cultivation/fermentation methods, variability in charging of bioreactors, sampling variations, and other factors. All of these factors can contribute to poor product yields and irreproducibility in the process, which have many attendant negative results from validation, legal, and operational standpoints. Therefore, multivariate quality control using methods like SimI is essential to developing reproducible production processes.

An effective implementation of SimI coupled with multidimensional fluorescence measurements for monitoring and control of production processes can yield the following benefits:

1) Rapid qualitative and quantitative analysis of aqueous based materials,
2) Rapid and continual analysis (online) of all material produced.
3) Automated analysis of material quality.
4) Immediate warning if a newly manufactured lot is out normal specification;
5) Allow for facile correlation of product quality to process parameters.

Successful bioprocess production means being able to maintain product media (e.g. feed, growth, and process) with a high degree of reproducibility from lot-to-lot, a good understanding of process capability and a possible minimization of product variation.

In practical usage where there may be insufficient samples available initially, it is proposed to use the median operation to extract the reference spectrum and to calculate the SimI values for investigating the variability and consistency of the sample class (cell culture media, raw materials, etc.). As more lots are manufactured (and samples become available) for a given process, and if discrimination data is available (e.g. performance data on media, yield, etc. . . . ), then the SimI model may be recursively updated. For example, when sufficient samples of good media have been acquired, the SimI method will become stable for diagnosing out-of-normal lot and tracking long-term quality performance.

The SimI method of the present invention provides for qualitative and quantitative assessment of comparatively complex aqueous media and for their compositional consistency by means of fluorescence EEM and TSFS data. It successfully addresses the resultant variance in the fluorescence topographies in a simply, rapid, and effective manner. There is a promising prospect for this technique to be used for multivariate quality control of batch bioprocesses.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A non-transitory computer readable medium having computer instructions stored therein, which when executed by a computer processor performs a method for determining the similarity between a first multivariate data set and a second multivariate data set comprising:
   i) representing the data of each multivariate data set in matrix form to yield a multivariate data matrix, wherein each multivariate data matrix has the same dimensions;
   ii) calculating the magnitude of an additive and subtractive combination of each multivariate data matrix;
   iii) introducing a penalty parameter to set a detectable limit of variance between said first multivariate data set and said second multivariate data set, and
   using said penalty parameter in combination with the results of step ii) to determine a similarity value;

wherein said determined similarity value indicates the variance between said first multivariate data set and said second multivariate data set.

2. A non-transitory computer readable medium according to claim 1 wherein step ii) comprises calculating the entrywise p-norm of an additive and subtractive combination of each multivariate data matrix, wherein $p \geq 1$.

3. A non-transitory computer readable medium according to claim 2 wherein p=1 or p=2.

4. A non-transitory computer readable medium according to claim 2 wherein the similarity value is determined by:
   a) multiplying the penalty parameter by the entrywise p-norm of a subtractive combination of the multivariate data matrices;
   b) subtracting the result of step a) from the entrywise p-norm of an additive combination of the multivariate data matrices; and
   c) dividing the result of step b) by the entrywise p-norm of an additive combination of the multivariate data matrices.

5. A non-transitory computer readable medium according to claim 4 wherein the data are discrete representations of multivariate observations.

6. A non-transitory computer readable medium according to claim 5 wherein the entrywise p-norm is computed as a summation.

7. A non-transitory computer readable medium according to claim 1 wherein the penalty parameter is expressed as a function of a threshold similarity value and said detectable limit of variance between said first multivariate data set and said second multivariate data set.

8. A non-transitory computer readable medium according to claim 7 wherein the penalty parameter is determined by:
   a) subtracting a threshold similarity value from the integer 1;
   b) selecting a detectable limit of variance between said first multivariate data set and said second multivariate data set;
   c) adding the detectable limit of variance to the integer 2, and dividing the result by the detectable limit of variance; or
   d) subtracting the detectable limit of variance from the integer 2, and dividing the result by the detection limit of variance; and
   e) multiplying the results of steps a) and c) or multiplying the results of steps a) and d).

9. A non-transitory computer readable medium according to claim 1 wherein the similarity value is determined by:
   a) multiplying the penalty parameter by the magnitude of a subtractive combination of the multivariate data matrices;
   b) subtracting the result of step a) from the magnitude of an additive combination of the multivariate data matrices; and
   c) dividing the result of step b) by the magnitude of an additive combination of the multivariate data matrices.

10. A non-transitory computer readable medium according to claim 1 wherein the multivariate data sets comprise spectroscopy multivariate data sets, chromatographic multivariate data sets or imaging multivariate data sets.

11. A non-transitory computer readable medium according to claim 1 wherein the multivariate data sets comprises fluorescence spectroscopy multivariate data sets.

12. A non-transitory computer readable medium according to claim 11 wherein the multivariate fluorescence spectroscopy data sets are selected from the group consisting of Fluorescence Excitation-Emission Matrix data sets, Total Synchronous Fluorescence Scanning data sets, or Time-Resolved Fluorescence Emission Spectra data sets.

13. A non-transitory computer readable medium according to claim 11 wherein the multivariate fluorescence spectroscopy data sets have been processed to correct the effects of Rayleigh scattering, Raman scattering and combinations thereof.

14. A non-transitory computer readable medium according to claim 11 wherein the step of calculating the magnitude of an additive and subtractive combination of each multivariate data matrix comprises calculating the entrywise p-norm of an additive and subtractive combination of each multivariate data matrix, wherein $p \geq 1$.

15. A non-transitory computer readable medium according to claim 14 wherein p=1 or p=2.

16. A non-transitory computer readable medium according to claim 11 wherein the penalty parameter is expressed as a function of a threshold similarity value and said detectable limit of variance between said first multivariate data set and said second multivariate data set.

17. A non-transitory computer readable medium according to claim 16 wherein the penalty parameter is determined by:
   a) subtracting a threshold similarity value from the integer 1;
   b) selecting a detectable limit of variance between said first multivariate data set and said second multivariate data set;
   c) adding the detectable limit of variance to the integer 2, and dividing the result by the detectable limit of variance; or
   d) subtracting the detection limit of variance from the integer 2, and dividing the result by the detection limit of variance; and
   e) multiplying the results of steps a) and c) or multiplying the results of steps a) and d).

18. A non-transitory computer readable medium according to claim 11 wherein the value of the penalty parameter is selected from 0.5, 1, 2, 3, 4, 5, 6 or 8.

19. A non-transitory computer readable medium according to claim 11 wherein the similarity value is determined by:
   a) multiplying the penalty parameter by the 2-norm of a subtractive combination of the multivariate data matrices;
   b) subtracting the result of step a) from the 2-norm of an additive combination of the multivariate data matrices;
   c) dividing the result of step b) by the 2-norm of an additive combination of the multivariate data matrices.

20. A non-transitory computer readable medium according to claim 19 wherein the data are discrete representations of multivariate observations.

21. A non-transitory computer readable medium according to claim 20 wherein the 2-norm is computed as a double summation.

* * * * *